United States Patent
Gunnoe et al.

(10) Patent No.: US 10,450,259 B2
(45) Date of Patent: Oct. 22, 2019

(54) COMPOSITIONS AND METHODS FOR HYDROCARBON FUNCTIONALIZATION

(71) Applicants: University of Virginia Patent Foundation, Charlottesville, VA (US); The Trustees of Princeton University, Princeton, NJ (US)

(72) Inventors: Thomas Brent Gunnoe, Palmyra, VA (US); George Fortman, Phoenixville, PA (US); Nicholas C. Boaz, Ewing, NJ (US); John T. Groves, Princeton, NJ (US)

(73) Assignees: University of Virginia Patent Foundation, Charlottesville, VA (US); The Trustees of Princeton University, Princeton, NJ (US)

(*) Notice: Subject to any disclaimer, the term of this patent is extended or adjusted under 35 U.S.C. 154(b) by 0 days.

(21) Appl. No.: 16/119,125

(22) Filed: Aug. 31, 2018

(65) Prior Publication Data
US 2019/0062255 A1  Feb. 28, 2019

Related U.S. Application Data

(63) Continuation-in-part of application No. 15/432,380, filed on Feb. 14, 2017, now abandoned, which is a
(Continued)

(51) Int. Cl.
*C07C 67/035* (2006.01)
*B01J 19/24* (2006.01)
(Continued)

(52) U.S. Cl.
CPC ............. *C07C 67/035* (2013.01); *B01J 19/24* (2013.01); *C07C 17/00* (2013.01); *C07C 19/00* (2013.01); *C07C 19/03* (2013.01); *C07C 19/043* (2013.01); *C07C 29/00* (2013.01); *C07C 29/147* (2013.01); *C07C 69/14* (2013.01); *C07C 69/63* (2013.01);
(Continued)

(58) Field of Classification Search
CPC ....... C07C 67/035; C07C 29/00; C07C 29/03; C07C 29/48; C07C 29/147; C07C 27/10; C07C 45/33; C07C 17/00; C07C 19/00; B01J 2219/00051; B01J 19/24
See application file for complete search history.

(56) References Cited

U.S. PATENT DOCUMENTS

| | | |
|---|---|---|
| 4,511,745 A | 4/1985 | Bergman |
| 5,387,397 A | 2/1995 | Strauss |
| 7,915,459 B2 | 3/2011 | Periana |

FOREIGN PATENT DOCUMENTS

| | | |
|---|---|---|
| WO | 99/24383 | 5/1999 |

OTHER PUBLICATIONS

International Search Report for PCT/US2014/044272 dated Oct. 16, 2014.
(Continued)

*Primary Examiner* — Yate' K Cutliff
(74) *Attorney, Agent, or Firm* — Thomas Horstemyer, LLP

(57) ABSTRACT

Embodiments of the present disclosure provide for methods of hydrocarbon functionalization, methods and systems for converting a hydrocarbon into a compound including at least one group ((e.g., hydroxyl group) (e.g., methane to methanol)), functionalized hydrocarbons, and the like. Systems and methods as described herein can utilize photocatalysis.

20 Claims, 10 Drawing Sheets

Related U.S. Application Data continuation of application No. 14/900,621, filed as application No. PCT/US2014/044272 on Jun. 26, 2014, now Pat. No. 9,604,890.

(60) Provisional application No. 61/839,415, filed on Jun. 26, 2013, provisional application No. 61/993,713, filed on May 15, 2014.

(51) Int. Cl.

| | |
|---|---|
| *C10L 1/02* | (2006.01) |
| *C07C 69/63* | (2006.01) |
| *C07C 29/147* | (2006.01) |
| *C07C 19/03* | (2006.01) |
| *C07C 19/043* | (2006.01) |
| *C07C 17/00* | (2006.01) |
| *C07C 19/00* | (2006.01) |
| *C07C 69/14* | (2006.01) |
| *C07C 29/00* | (2006.01) |
| *C07C 29/03* | (2006.01) |
| *C07C 29/48* | (2006.01) |

(52) U.S. Cl.
CPC ........ *C10L 1/02* (2013.01); *B01J 2219/00051* (2013.01); *B01J 2219/24* (2013.01); *C07C 29/03* (2013.01); *C07C 29/48* (2013.01); *C07C 2602/42* (2017.05); *C07C 2603/74* (2017.05)

(56) References Cited

OTHER PUBLICATIONS

Smegal et al., Hydrocarbon functionalization byt he (Iodosylbenzene)manganese (IV) Porphyrin complexes from the (Tetraphenylporphinato)manganese (III)-Iodosylbenzene catalytic hydrocarbon oxidation system, Mechanism and Reaction Chemistry, 1983, J. Am Chem Soc., vol. 105, pp. 3515-3521.

Kendall, D.C., et al., Chemical Reactors: Basic Control Strategies, 2006, Process Control Optimization, vol. II, ED. B. G. Liptak, Ch. 8, Section 8.9 (100 pages).

Marnasidou, K.G., et al., Catalytic partial oxidation of methane to synthesis gas in a pilot-plant-scale spouted-bed reactor, 1999, Chem. Engr. Sci., vol. 54, pp. 3691-3699.

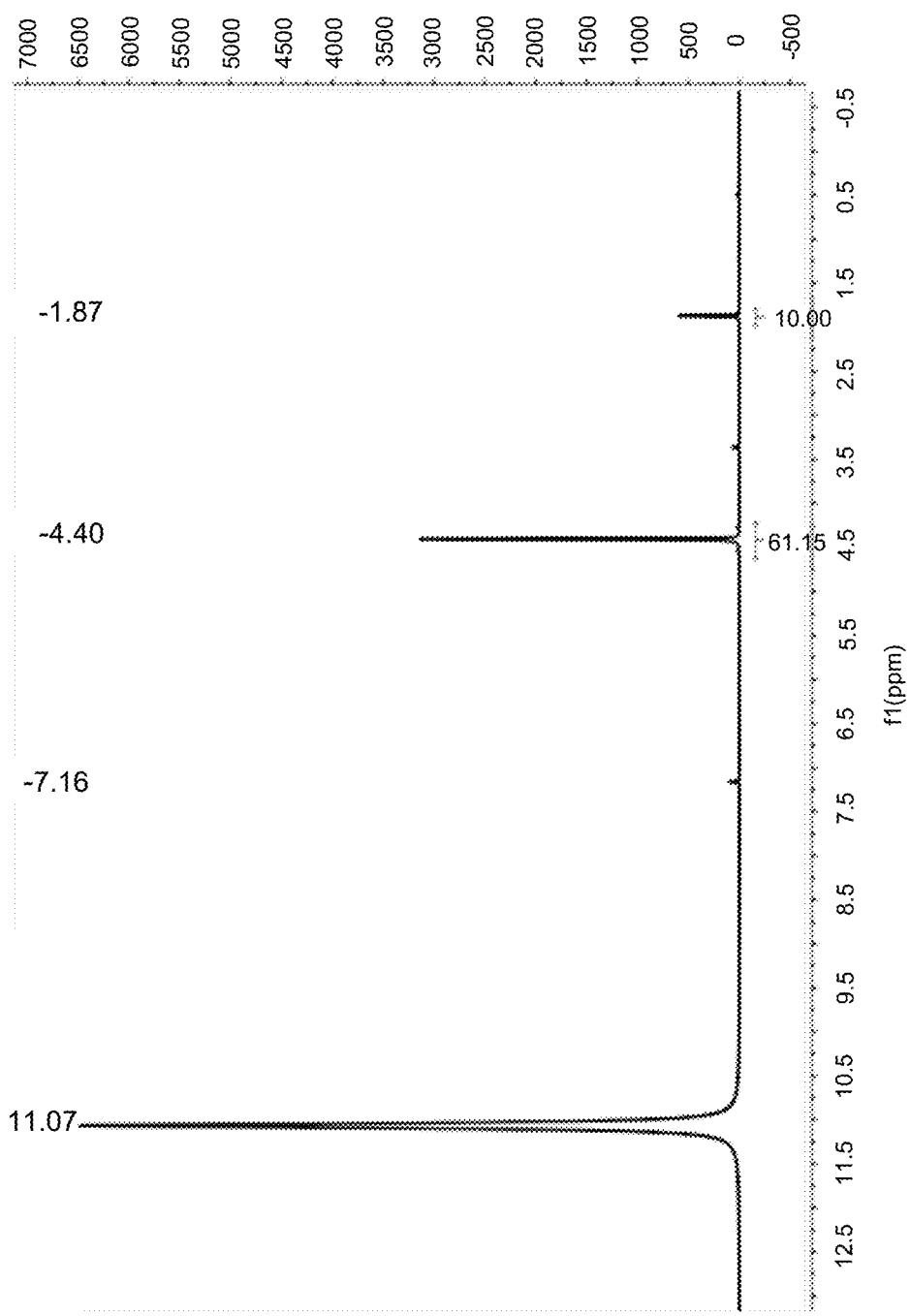
FIG. 1.1

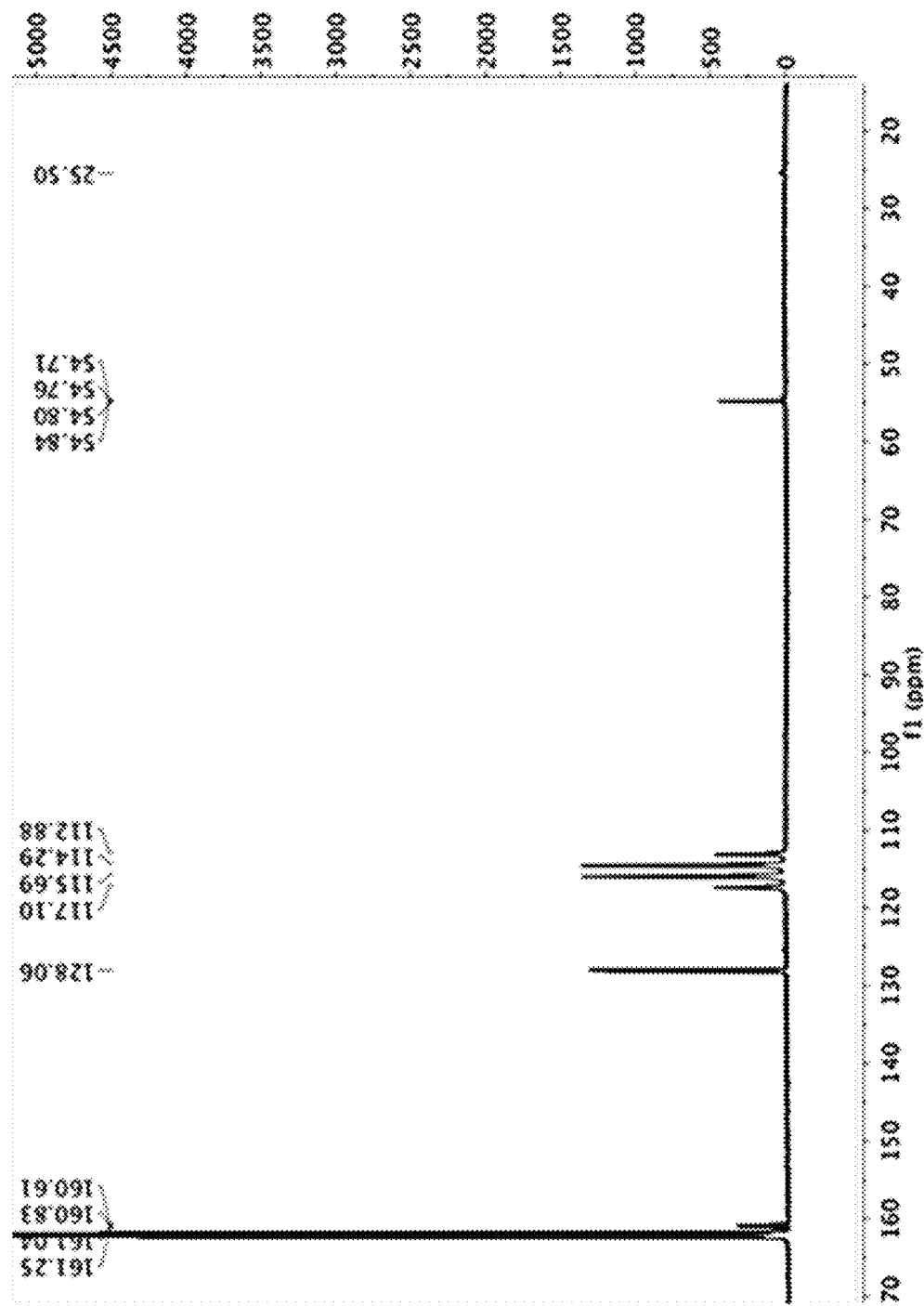
FIG. 1.2

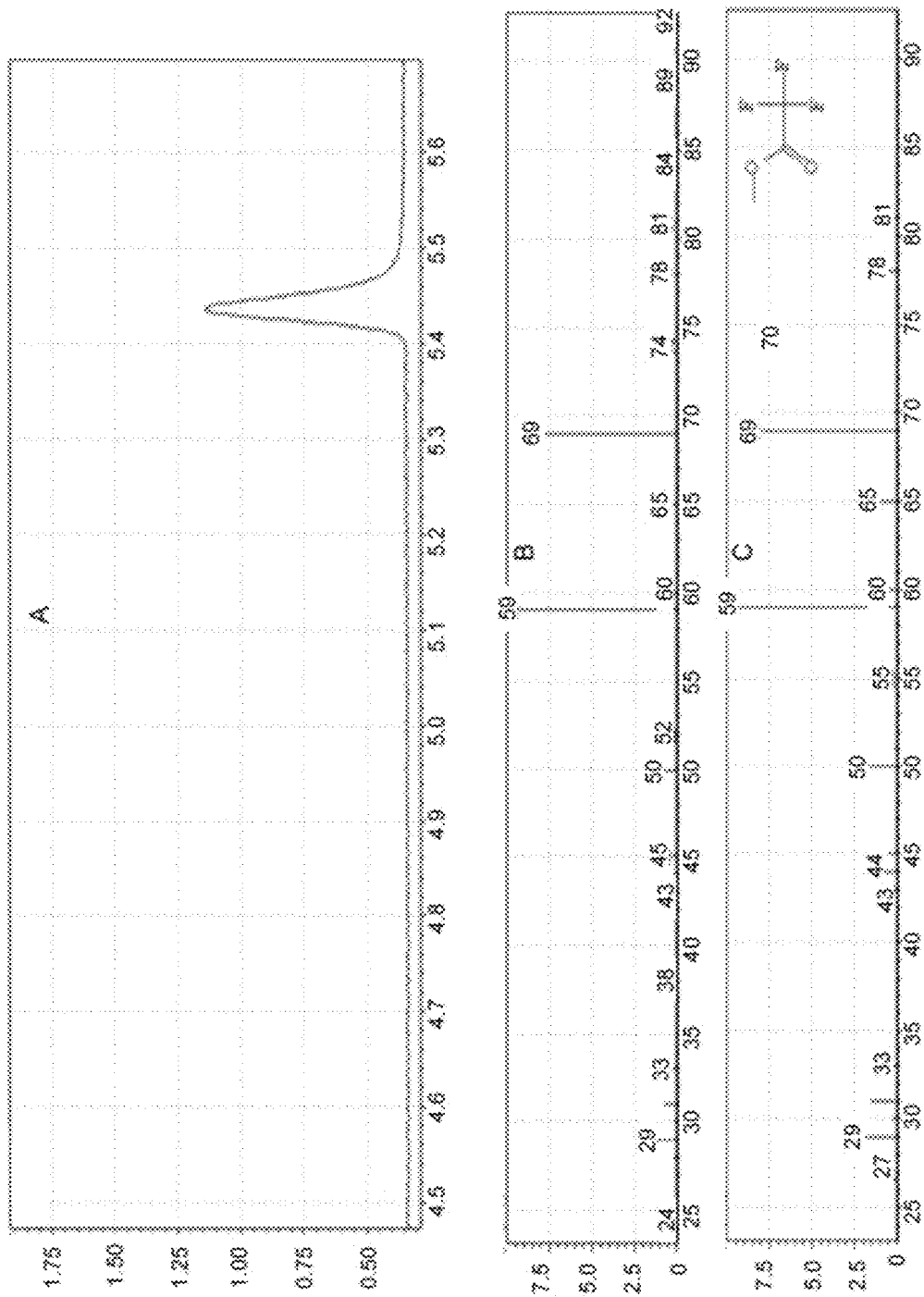
FIG. 1.3

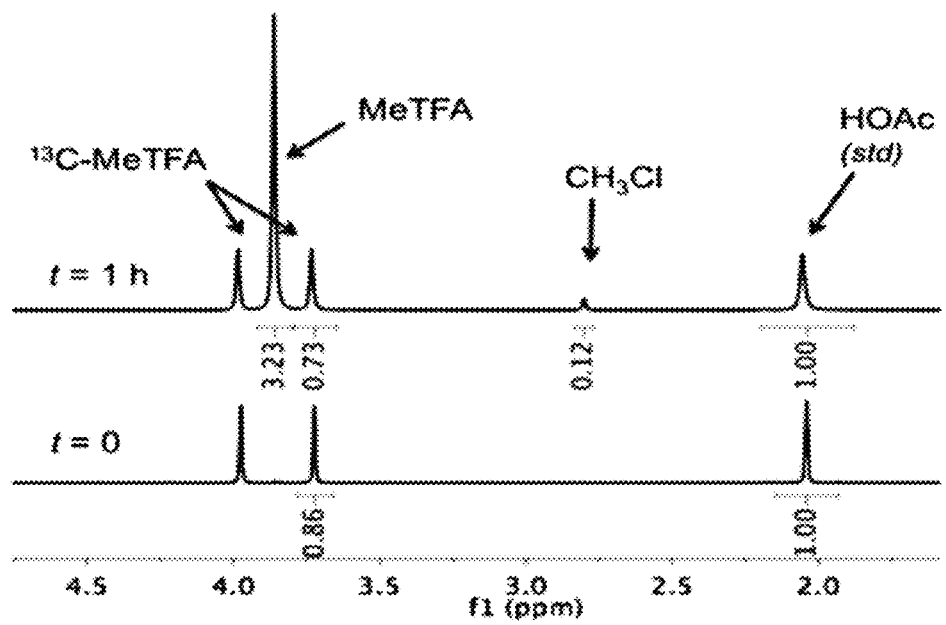
FIG. 2.1
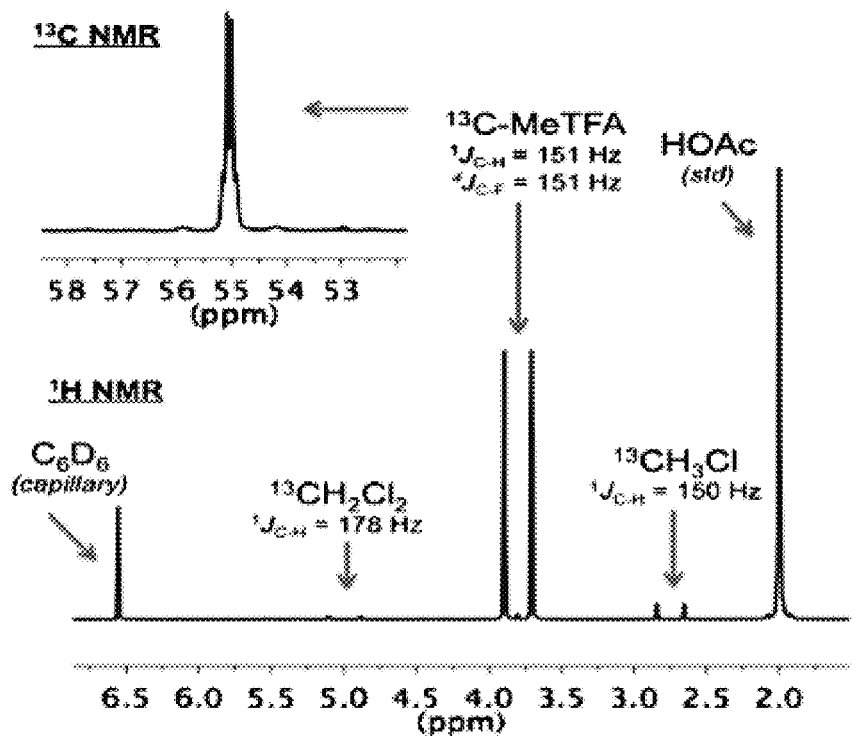
FIG. 2.2

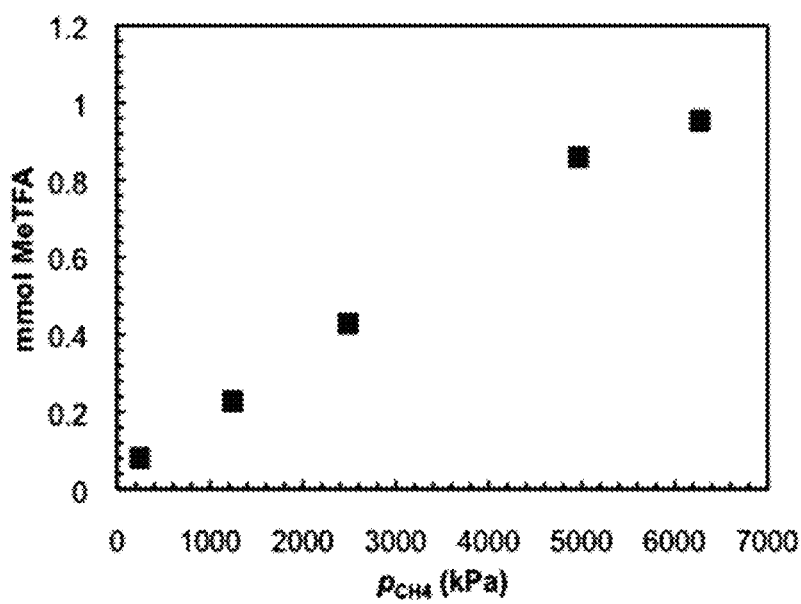
FIG. 2.3
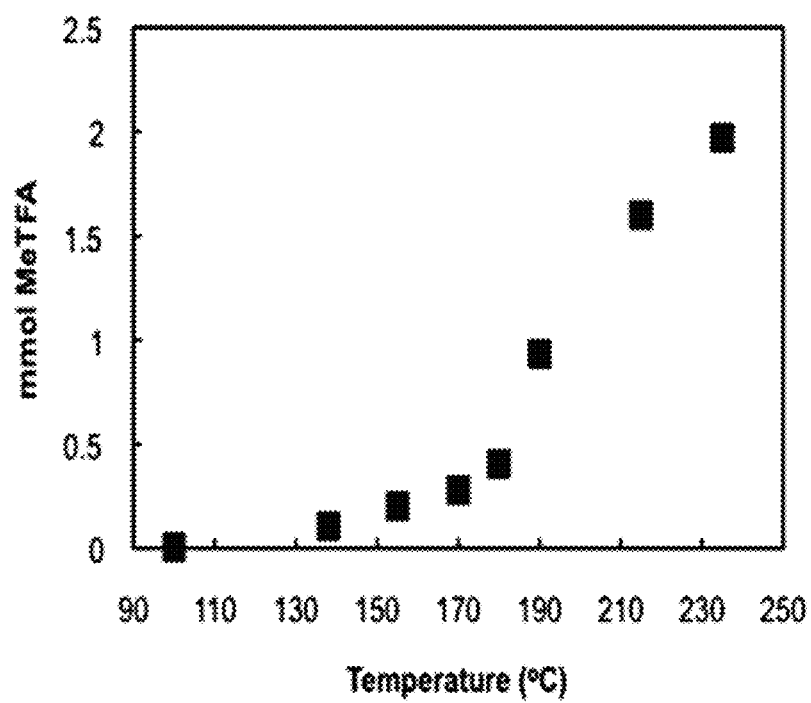
FIG. 2.4

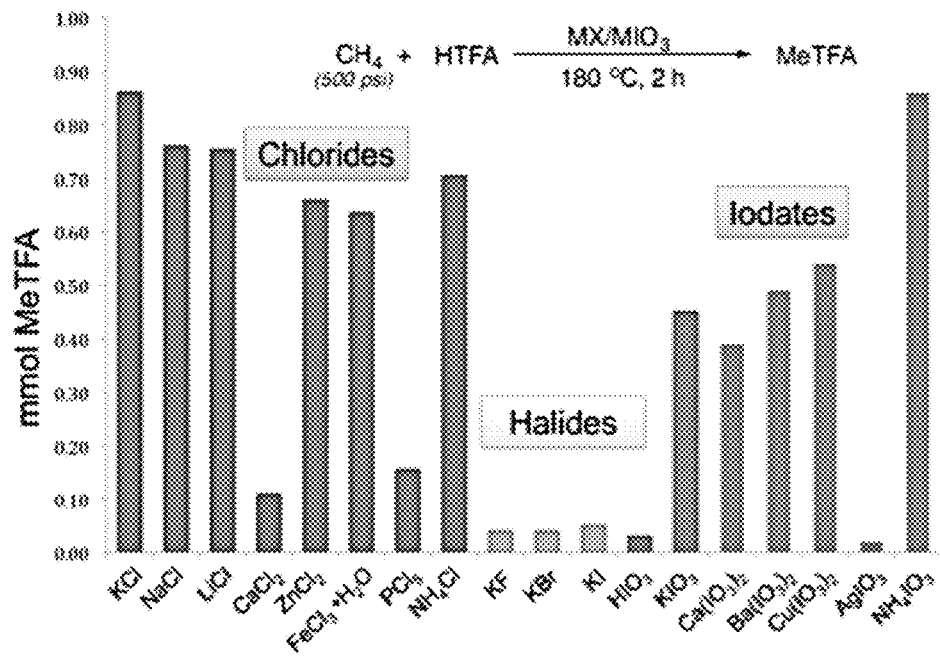
FIG. 2.5
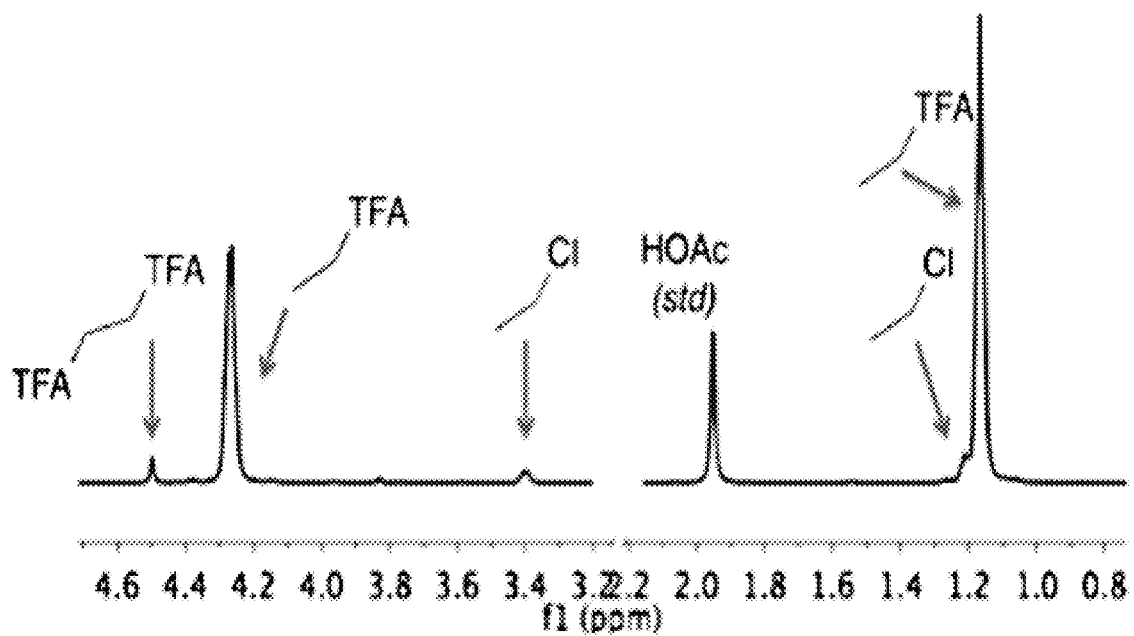
FIG. 2.6

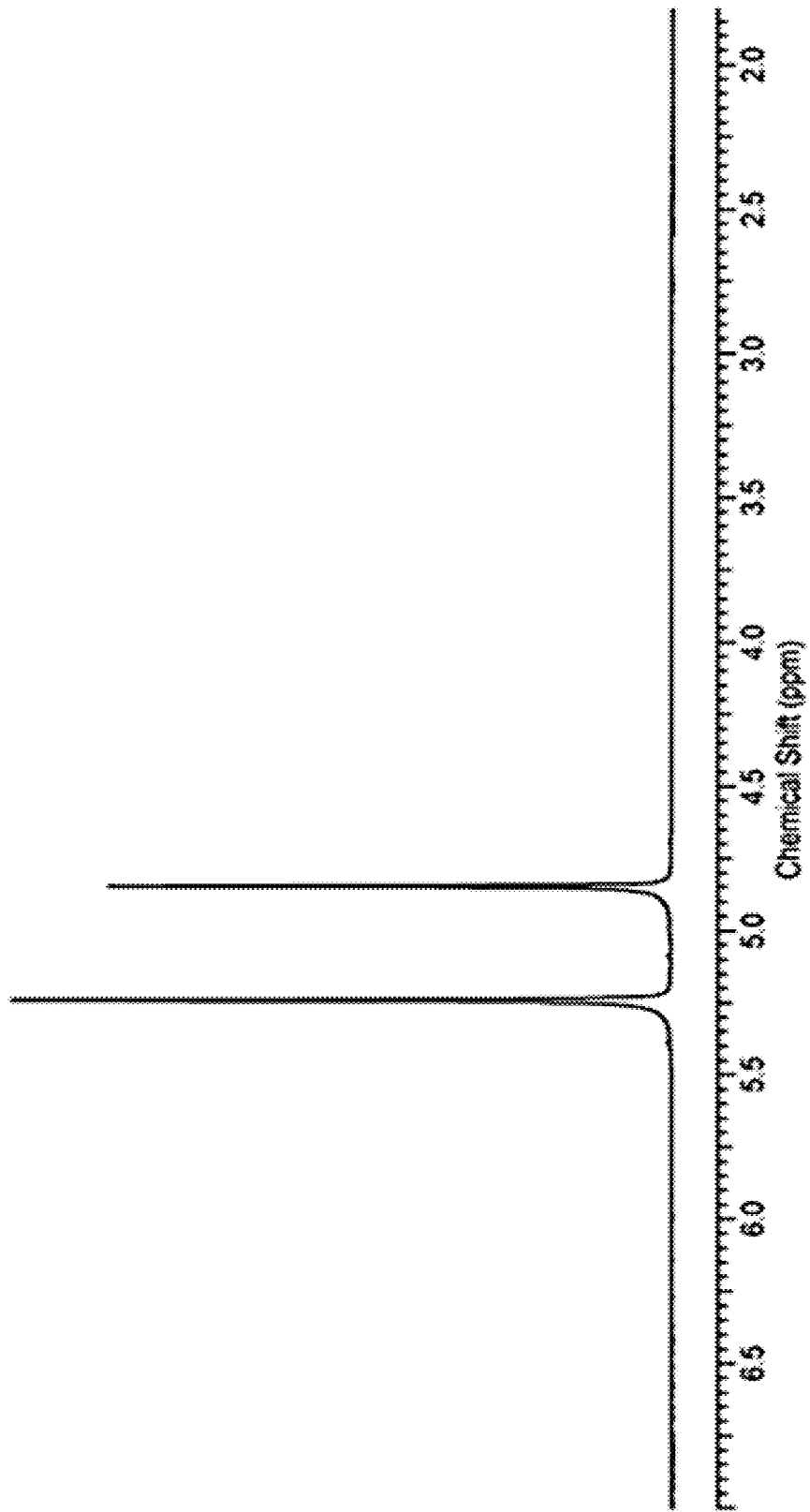
FIG. 3.1

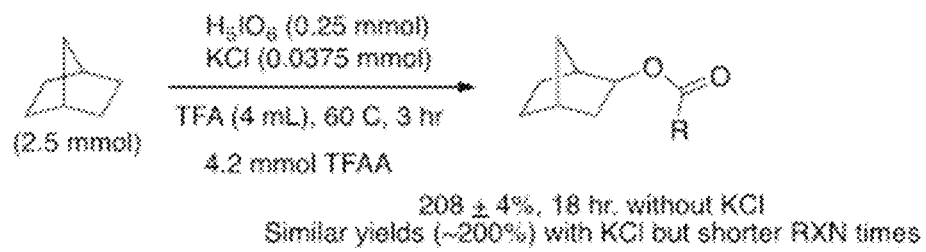
FIG. 4.1
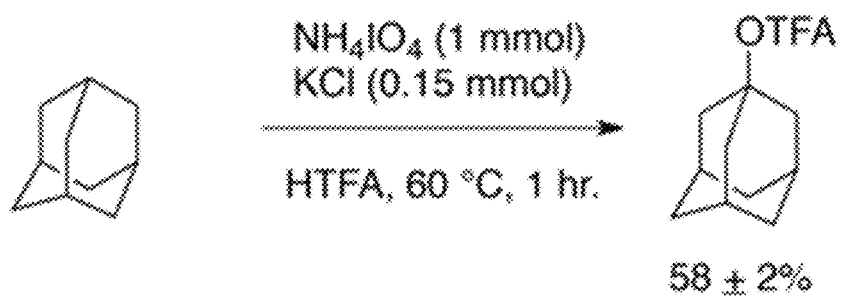
FIG. 5.1

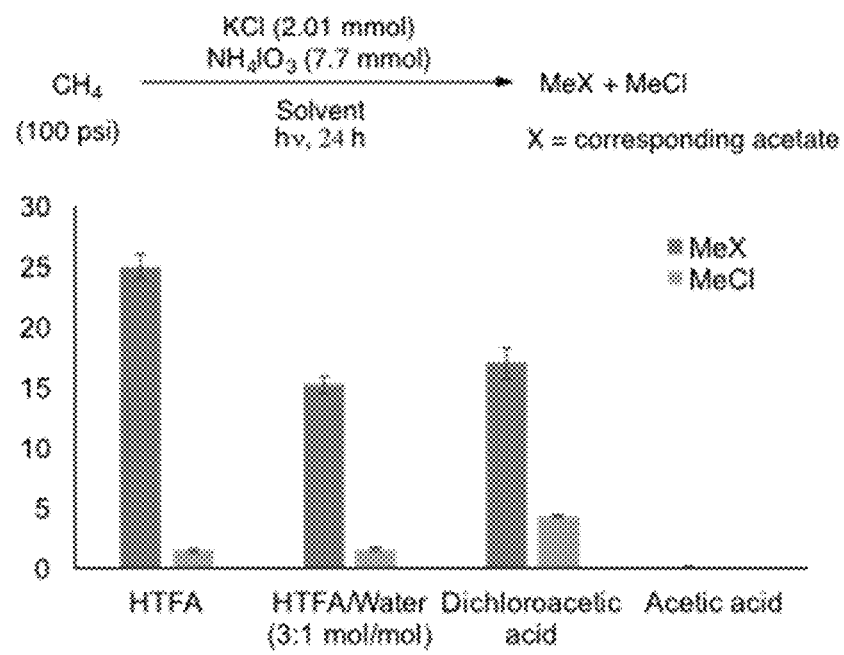
FIG. 6.1
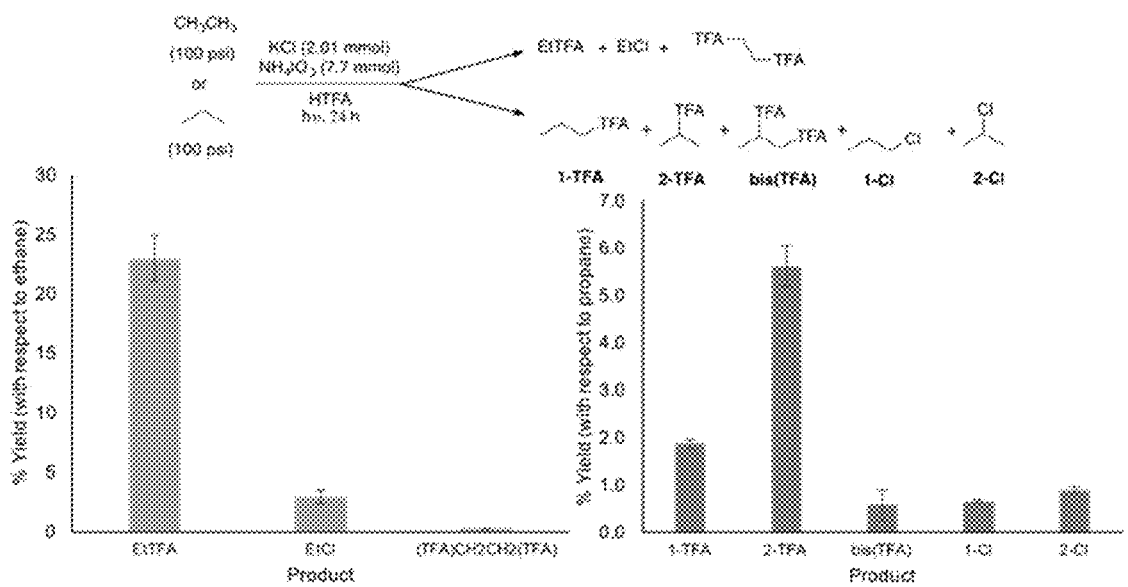
FIG. 7.1

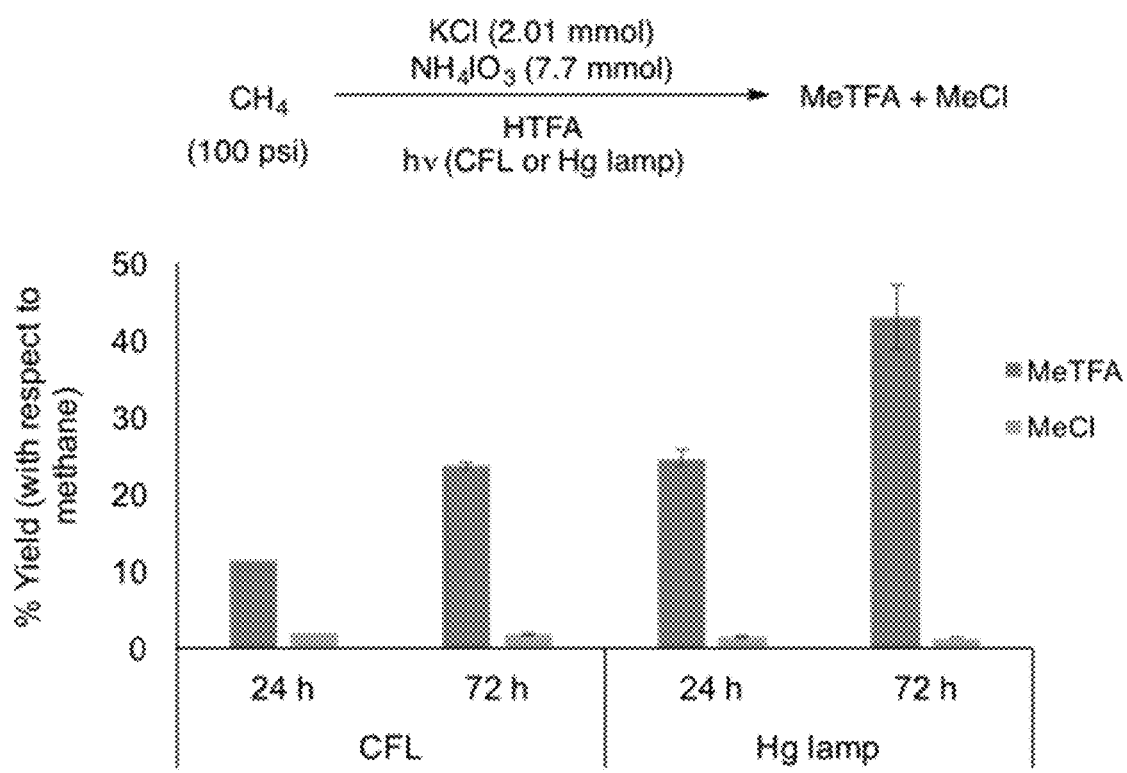
FIG. 8.1

COMPOSITIONS AND METHODS FOR HYDROCARBON FUNCTIONALIZATION

CROSS-REFERENCE TO RELATED APPLICATION

This application is a continuation-in-part of, and claims priority to, co-pending U.S. Patent application entitled "COMPOSITIONS AND METHODS FOR HYDROCARBON FUNCTIONALIZATION," having Ser. No. 15/432,380 and filed in the United States on Feb. 14, 2017, which is entirely incorporated herein by reference. U.S. Patent application having Ser. No. 15/432,380 is a continuation of, and claims priority to, U.S. application entitled "COMPOSITIONS AND METHODS FOR HYDROCARBON FUNCTIONALIZATION," having Ser. No. 14/900,621 and filed in the United States on Dec. 22, 2015 (now U.S. Pat. No. 9,604,890), which is entirely incorporated herein by reference. U.S. Patent application, having Ser. No. 14/900,621, is the 35 U.S.C. § 371 national stage application of PCT Application No. PCT/US2014/044272, filed Jun. 26, 2014, which is entirely incorporated herein by reference. PCT/US2014/044272 claims priority to U.S. provisional application entitled "COMPOSITIONS AND METHODS FOR HYDROCARBON FUNCTIONALIZATION," having Ser. No. 61/839,415, filed on Jun. 26, 2013, which is entirely incorporated herein by reference. PCT/US2014/044272 also claims priority to U.S. provisional application entitled "COMPOSITIONS AND METHODS FOR HYDROCARBON FUNCTIONALIZATION," having Ser. No. 61/993,713, filed on May 15, 2014, which is entirely incorporated herein by reference.

FEDERAL SPONSORSHIP

This invention was made with government support under Grant No. DE-SC0001298, awarded by The United States Department of Energy. The government has certain rights in the invention.

BACKGROUND

Hydrocarbons, molecules composed entirely of carbon and hydrogen, are the predominant components of fossil resources including coal, petroleum, and natural gas. The conversion of raw hydrocarbons derived from fossil resources is fundamental to the energy sector as well as the petrochemical sector. One of the more challenging classes of hydrocarbons to convert to higher value compounds and fuels is derived from natural gas, which is composed predominately of alkanes, mostly methane ($CH_4$) but also ethane ($C_2H_6$), propane ($C_3H_8$), and butane ($C_4H_{10}$). Current methods to convert the alkanes from natural gas into higher value compounds (including olefins and liquid fuel such as methanol) involve processes that are energy intensive. For example, the conversion of methane to methanol (a liquid fuel and useful chemical precursor) provides a viable route to transition natural gas into liquid fuel and high value chemicals, but the transformation of methane into methanol by current technologies requires methane reforming to generate carbon monoxide and dihydrogen (known as "synthesis" or syn gas) followed by Fischer-Tropsch catalysis. For the formation of olefins, high temperature "cracking" is required. These processes require high temperature and pressure, and the infrastructure (including the chemical plants and infrastructure to deliver natural gas) for them is very expensive.

Despite the recent increase in natural gas availability and reduction in expense, scaled use of natural gas as a fuel for the transportation sector or a feedstock for the petrochemical industry has been limited by the expense of the infrastructure for the processing plants and for movement of natural gas. Thus, there is a need to overcome these challenges.

SUMMARY

Embodiments of the present disclosure provide for methods of hydrocarbon functionalization, methods and systems for converting a hydrocarbon into a compound including at least one group (e.g., hydroxyl group) (e.g., methane to methanol), functionalized hydrocarbons, and the like.

An embodiment of the method includes, among others, includes mixing $A_aX_n$, an iodine-based compound, and a source of functionalization to form a first mixture, wherein A is selected from the group consisting of: hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$) and a combination thereof, wherein X is chlorine or bromine, wherein subscript "a" is an oxidation state of X and subscript "n" is an oxidation state of A;

mixing the first mixture with a hydrocarbon in the gas phase to form a second mixture; and applying light from a light source to the second mixture to make a functionalized hydrocarbon.

Also described herein are systems for producing a functionalized hydrocarbon. In an embodiment, a system for producing a functionalized hydrocarbon can comprise a vessel including $A_aX_n$, an iodine-based compound, and a source of functionalization to form a first mixture and a hydrocarbon. A can be hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$) and a combination thereof. X can be chlorine or bromine. "a" is the oxidation state of X and "n" is the oxidation state of A. The vessel further comprises a light source. In certain aspects, the light source can be a mercury arc lamp or a compact fluorescent light bulb

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1 illustrates a $^1H$ NMR spectrum (HTFA—$C_6D_6$ insert; 600 MHz) from the reaction in example 1 with a cyclopentane standard added and $C_6D_6$ insert. 11.07 ppm—trifluoroacetic acid, 7.16 ppm—benzene-$d_6$ insert, 4.40 ppm—methyl trifluoroacetic ester, 1.87 ppm—cyclopentane standard.

FIG. 1.2 illustrates a $^{13}C$ NMR spectrum (HTFA—$C_6D_6$ insert; 200 MHz) from the reaction of example 1 with a cyclopentane standard added. MeTFA δ (ppm): 160.9 (q, $^2J_{CF}$=43 Hz, C=O), 115.0 (overlap with HTFA, q, $^1J_{CF}$=283 Hz, $CF_3$), 54.8 (q, $^3J_{CF}$=8.9 Hz, $CH_3$).

FIG. 1.3 illustrates a GC-MS plot of a reaction from example 1: (A) Mass count response. Elution time of MeTFA=5.43. (B) Mass spectrum (with subtracted background) at t=5.43. (C) Mass spectrum of methyl trifluoromethylacetate ester from 2008 NIST library.

FIG. 2.1 illustrates $^1$H NMR spectra resulting from the partial oxidation of methane when $^{13}$C-MeTFA was added to the initial reaction mixture (bottom spectrum B). At least 85% of $^{13}$C-MeTFA was retained over 1 h (top spectrum A). Conditions: 0.90 mmol $^{13}$C-MeTFA; 0.676 mmol KCl; 7.7 mmol NH$_4$IO$_3$; 8.0 mL HTFA; $p_{CH4/Ne}$=3450 kPa (8.4 mmol CH$_4$); 800 rpm; 180° C.; 1 h.

FIG. 2.2 illustrates $^1$H NMR and $^{13}$C NMR spectra of a reaction mixture starting with $^{13}$CH$_4$. Conditions: 0.17 mM KCl; 1.13 mM KIO$_3$; 2.0 mL HTFA; $p_{CH4}$=240 kPa; total pressure filled to 5520 kPa with Ar; 180° C.; 2 h; 600 rpm.

FIG. 2.3 illustrates the production of MeTFA as a function of initial methane pressure. Conditions: 0.338 mmol KCl; 2.26 mmol KIO$_3$; 2.0 mL HTFA; 180° C.; 2 h; 600 rpm.

FIG. 2.4 illustrates MeTFA production as a function of temperature. Conditions: 0.676 mmol KCl; 7.7 mmol NH$_4$IO$_3$; 8.0 mL HTFA; $p_{CH4/Ne}$=3450 kPa (8.4 mmol CH$_4$); 800 rpm; 20 min.

FIG. 2.5 illustrates a comparison of halides, chloride sources and iodate sources for the partial oxidation of methane. Conditions: 0.338 mmol X$^-$; 2.26 mmol IO$_3^-$; 2.0 mL HTFA; $p_{CH4/Ne}$=5520 kPa; 180° C.; 2 h; 600 rpm. NH$_4$IO$_3$ was used as the oxidant for the reactions involving M$^{n+}$Cl$_n$ and KX. KCl was used in the reactions involving M$^{n+}$(IO$_3$)$_n$.

FIG. 2.6 illustrates a $^1$H NMR spectrum from reaction of C$_2$H$_6$ with HTFA in the presence of NH$_4$IO$_3$ and KCl. Conditions: 0.676 mmol KCl; 7.7 mmol NH$_4$IO$_3$; 8.0 mL HTFA; $p_{C2H6}$=2070 kPa; 180° C.; 1 h; 800 rpm.

FIG. 3.1 illustrates a $^1$H NMR spectrum of a reaction mixture, measured in trifluoroacetic acid with capillary containing benzene-D$_6$. 5.2 ppm: dichloromethane, 4.8 ppm: methyltrifluoroacetate.

FIG. 4.1 is a scheme that illustrates the oxidation of norbornane using H$_5$IO$_6$ as the oxidant with catalytic KCl. Note that yields presented are relative to the amount of iodine(VII) and are the average of the reaction run at least 3 times.

FIG. 5.1 is a scheme that illustrates the oxidation of adamantane using ammonium periodate and catalytic potassium chloride. The yields presented are relative to the amount of adamantane in solution.

FIG. 6.1 is a graph illustrating the effect of solvent on photolytic methane functionalization.

FIG. 7.1 is a schematic showing photolytic functionalization of ethane and propane with iodate and chloride salts.

FIG. 8.1 shows photolytic functionalization of methane using CFL or a Hg arc lamp.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

Different stereochemistry is also possible, such as products of syn or anti addition could be both possible even if only one is drawn in an embodiment.

It must be noted that, as used in the specification and the appended claims, the singular forms "a," "an," and "the" include plural referents unless the context clearly dictates otherwise. Thus, for example, reference to "a support"

includes a plurality of supports. In this specification and in the claims that follow, reference will be made to a number of terms that shall be defined to have the following meanings unless a contrary intention is apparent.

Definitions

By "chemically feasible" is meant a bonding arrangement or a compound where the generally understood rules of organic structure are not violated. The structures disclosed herein, in all of their embodiments are intended to include only "chemically feasible" structures, and any recited structures that are not chemically feasible, for example in a structure shown with variable atoms or groups, are not intended to be disclosed or claimed herein.

The term "substituted" refers to any one or more hydrogen atoms on the designated atom (e.g., a carbon atom) that can be replaced with a selection from the indicated group (e.g., halide, hydroxyl, alkyl, and the like), provided that the designated atom's normal valence is not exceeded.

As used herein, an "analog", or "analogue" of a chemical compound is a compound that, by way of example, resembles another in structure but is not necessarily an isomer (e.g., 5-fluorouracil is an analog of thymine).

As used herein, a "derivative" of a compound refers to a chemical compound that may be produced from another compound of similar structure in one or more steps, as in replacement of H by an alkyl, acyl, or amino group.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "alkane" refers to a saturated aliphatic hydrocarbon which can be straight or branched, having 1 to 40, 1 to 20, 1 to 10, or 1 to 5 carbon atoms, where the stated range of carbon atoms includes each intervening integer individually, as well as sub-ranges. Examples of alkane include, but are not limited to methane, ethane, propane, butane, pentane, and the like. Reference to "alkane" includes unsubstituted and substituted forms of the hydrocarbon.

As used herein, "alkyl" or "alkyl group" refers to a saturated aliphatic hydrocarbon radical which can be straight or branched, having 1 to 40, 1 to 20, 1 to 10, or 1 to 5 carbon atoms, where the stated range of carbon atoms includes each intervening integer individually, as well as sub-ranges. Examples of alkanes include, but are not limited to methyl, ethyl, n-propyl, i-propyl, n-butyl, s-butyl, t-butyl, n-pentyl, and s-pentyl. Reference to "alkyl" or "alkyl group" includes unsubstituted and substituted forms of the hydrocarbon group.

As used herein, "alkene" refers to an aliphatic hydrocarbon which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkene groups include, but are not limited to, ethene, propene, and the like. Reference to "alkene" includes unsubstituted and substituted forms of the hydrocarbon.

As used herein, "alkenyl" or "alkenyl group" refers to an aliphatic hydrocarbon radical which can be straight or branched, containing at least one carbon-carbon double bond, having 2 to 40, 2 to 20, 2 to 10, or 2 to 5 carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like. Reference to "alkyl" or "alkyl group" includes unsubstituted and substituted forms of the hydrocarbon group.

As used herein, "alkyne" refers to straight or branched chain hydrocarbon groups having 2 to 40, 2 to 20, 2 to 10, or 2 to 5 carbon atoms and at least one triple carbon to carbon bond. Reference to "alkyne" includes unsubstituted and substituted forms of the hydrocarbon.

As used herein, "alkynyl" or "alkynyl group" refers to straight or branched chain hydrocarbon groups having 2 to 40, 2 to 20, 2 to 10, or 2 to 5 carbon atoms and at least one triple carbon to carbon bond, such as ethynyl. Reference to "alkynyl" or "alkynyl group" includes unsubstituted and substituted forms of the hydrocarbon group.

As used herein, "aromatic" refers to a monocyclic or multicyclic ring system of 6 to 20 or 6 to 10 carbon atoms having alternating double and single bonds between carbon atoms. Exemplary aromatic groups include benzene, naphthalene, and the like. Reference to "aromatic" includes unsubstituted and substituted forms of the hydrocarbon.

As used herein, "aryl" or "aryl group" refers to an aromatic monocyclic or multicyclic ring system of 6 to 20 or 6 to 10 carbon atoms. The aryl is optionally substituted with one or more $C_1$-$C_{20}$ alkyl, alkylene, alkoxy, or haloalkyl groups. Exemplary aryl groups include phenyl or naphthyl, or substituted phenyl or substituted naphthyl. Reference to "aryl" or "aryl group" includes unsubstituted and substituted forms of the hydrocarbon group.

The term "substituted," as in "substituted alkyl", "substituted aryl," "substituted heteroaryl" and the like, means that the substituted group may contain in place of one or more hydrogens a group such as alkyl, hydroxy, amino, halo, trifluoromethyl, cyano, alkoxy, alkylthio, or carboxy.

As used herein, "halo", "halogen", "halide", or "halogen radical" refers to a fluorine, chlorine, bromine, iodine, and astatine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

As used herein, "cyclic" hydrocarbon refers to any stable 4, 5, 6, 7, 8, 9, 10, 11, or 12 membered, (unless the number of members is otherwise recited), monocyclic, bicyclic, or tricyclic cyclic ring.

As used herein, "heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which includes carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a heteroatom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring).

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

General Discussion

Embodiments of the present disclosure provide for methods of hydrocarbon functionalization, methods and systems for converting a hydrocarbon into a compound including at least one group ((e.g., hydroxyl group) (e.g., methane to methanol)), functionalized hydrocarbons, and the like.

Advantages of embodiments of the present disclosure can include: 1) the use of a simple and inexpensive catalyst (e.g., $A_aX_n$ such as sodium chloride (table salt)), 2) iodine-based compound oxidants that can be thermally regenerated using oxygen in air (e.g., iodate, periodate, I(III) reagents), 3) fast conversion of alkanes, 4) low temperatures (e.g., about 100 to 250° C.), 5) selectivity toward mono-functionalized product, and 6) the use of sources of functionalization (e.g., acids) that are more weakly acidic than oleum (e.g., trifluoroacetic acid, acetic acid, water) or halogens.

In an embodiment, alkanes can be converted to mono-functionalized esters in good yields with the use of salts (e.g., chloride salts (in catalytic amounts)) and with iodine-based compound as the sole oxidant in source of functionalization (e.g., iodate or periodate). In one aspect, the system operates over a large range of pressures (e.g., about 240-6900 kPa) and temperatures (e.g., about 100-235° C.) and at short reaction times (often about 2 hours or less) and exhibits excellent selectivity for monofunctionalized products. Embodiments of the present disclosure can provide for conversions of methane to MeTFA>20% (TFA=trifluoroacetate), conversion of ethane can be even more efficient with about 30% yield of EtTFA, and propane conversion can occur >20% yield. The values for alkane conversion disclosed herein meet many of the established benchmarks for efficient alkane functionalization. In addition, the distinct reactivity imparted by chloride (compared with $I_2$, $IO_3^-$, $I(TFA)_3$, etc. with no chloride) disclosed herein is unique and without precedent, resulting in substantial increases in efficiency for production of mono-functionalized alkanes. An additional benefit of the present disclosure is that iodine (e.g., the byproduct of KCl/$IO_3^-$ oxidation reactions) can be reoxidized to iodate in basic aqueous solution with molecular oxygen.

An embodiment of the present disclosure includes methods of making a compound including at least one group such as, but not limited to, hydroxyl, halide, carbonyl and a combination thereof (e.g., glycols, carboxylic acids), using hydrocarbons, such as those present in natural gas. In an embodiment, the compound including at least one group can include a combination of groups selected from hydroxyl, halide, or carbonyl. In an embodiment, the method can include mixing a salt ($A_aX_n$), an iodine-based compound, and a source of functionalization to form a first mixture and then mixing the first mixture with a hydrocarbon in the gas phase to make a functionalized hydrocarbon. Subsequently, the functionalized hydrocarbon can be converted to an alcohol, glycol, amine or a combination thereof and the source of functionalization, where the source of functionalization can be recycled.

In an embodiment, the salt, the iodine-based compound, and the source of functionalization can be added (e.g., separately, mixed prior to introduction and then added, or simultaneously added) to a reaction vessel to form a first mixture and then the hydrocarbon can be added to the reaction vessel. In an embodiment, the reaction vessel can be pressurized with a gas sufficient to provide an internal pressure of about 103 kPa (15 psi) to 10343 kPa (1500 psi) or about 240 kPa (35 psi) to 5516 kPa (800 psi) using a pressure system. In an embodiment, the gas used to obtain this pressure are methane, ethane, propane, butane, carbon dioxide, nitrogen, helium, argon, neon, carbon monoxide, hydrogen, oxygen, air, the hydrocarbon itself, or mixtures thereof. In an embodiment, the pressure system can include pumps, valves, metering gauges, computer system, and the like to accomplish flowing gas into and out of the vessel.

In an embodiment, the reaction vessel can be heated to a temperature of about 25 to 300° C. or about 130 to 230° C. using a temperature system. In an embodiment, the temperature system can include heating elements and a computer system to control the heat within the vessel. The temperature can be maintained over a period of about 10 minutes to 5 days or 20 minutes to 5 hours in order to contact the hydrocarbon with the salt, the iodine-based compound, the source of functionalization and pressurization gas to generate a mixture including the functionalized hydrocarbon formed from the hydrocarbon and an adduct of the source of functionalization. In an embodiment, the vessel can include a system to mix the contents of the vessel.

In an embodiment, the hydrocarbon can be aliphatic or aromatic, substituted or unsubstituted, having 1 to 40 carbon atoms. In an embodiment, the aliphatic hydrocarbon can be saturated or unsaturated, linear, branched, or cyclic. In an embodiment, the hydrocarbon can be a hydrocarbon that is in the gas phase at room temperature. In an embodiment, the hydrocarbon can be in a purified form or a mixture of multiple hydrocarbons (e.g., natural gas). An embodiment of the hydrocarbon can include methane, ethane, propane, butane, benzene, toluene, naphthalene, norbornane, adamantane and a mixture thereof.

In an embodiment, the compound including at least one hydroxyl group can be an alcohol or glycol of the hydrocarbons noted herein. For example, the compound can be methanol, ethanol, propanol, butanol, ethylene glycol, propylene glycol, and the like.

In an embodiment, the compound including at least one halide, can be chloromethane, iodomethane, chloroethane, 1,2-dichloroethane, iodoethane, 1,2-diiodoethane, chloropropane, 1,2-dichloropropane, 1,3-dichloropropane, iodopropane, 1,2-iodopropane, 1,3-diiodopropane and the like.

In an embodiment, the compound including at least one carbonyl group, can be a methyl ester, ethyl ester, propyl ester and the like.

In an embodiment, the alkane conversion can be about 15% to 30% with selectivity of up to about 98%, in a 1 or 2 hour reaction. For example, ethane can be converted to monofunctionalized ethyl product in about 30% conversion with about 98% selectivity. In another example, functionalized methyl product can be formed from methane with about 10% to 25% conversion with up to about 90% selectivity.

As noted above, the salt can be represented by $A_aX_n$. In an embodiment, "A" can represent an element or combination of elements capable of maintaining a formal positive charge. In an embodiment $A_aX_n$, can be a salt such as a halide salt. In an embodiment, "A" can be: hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$). In an embodiment, X can be chloride. In an embodiment, subscript "a" can represent the oxidation state of "X" and subscript "n" can represent the oxidation state of "A". In an embodiment $A_aX_n$, can be: HCl, NaCl, KCl, $CaCl_2$, LiCl, $ZnCl_2$, $BeCl_2$, $MgCl_2$, $PCl_3$, $NH_4Cl$, $CCO_4$, $CHCl_3$, transition metal chlorides, main group metal chlorides or organochlorides. These compounds are available for purchase from commercial suppliers, can be prepared from reported procedures, can be prepared in situ by reaction elements with halogen sources and from natural saline solutions.

In an embodiment, the iodine-based compound can include an iodate, periodate, iodine oxide (such as diiodine tetroxide, iodine monoxide, diiodine pentoxide, iodine monoxide or tetraiodine nonoxide), iodosyl ($IO^+$), trivalent iodine compound such $I(TFA)_3$, and a combination thereof. In an embodiment, the iodate can be represented by $Q(IO_3)_p$. In an embodiment "Q" can be: hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$). Subscript "p" can be 1 to 5.

In an embodiment, the iodine-based compound can include $Q_o(IO_4)_p$. In an embodiment "Q" can be hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$). Subscript "o" can be 1 and subscript "p" can be 1 to 5.

In an embodiment, the iodine-based compound can include $H_5(IO_6)$.

In particular, the iodine-based compound can be: $KIO_3$, $Ca(IO_3)_2$, $Ba(IO_3)_2$, $Cu(IO_3)_2$, $NH_4IO_3$, $KIO_4$, $NaIO_4$ and $NH_4IO_4$, $I(TFA)_3$, $I_2O_5$, $[IO]^+$, $[IO_2]^+$, and a combination thereof. The iodine-based compound, such as iodates, can be purchased commercially, prepared through reported procedures or generated in situ by means which include but are not limited to chemically, thermally, electrochemically, or though photolysis.

In an embodiment, the source of functionalization can include a solvent that can be used to functionalize the hydrocarbon. In an embodiment, the source of functionalization can be: trifluoroacetic acid, trifluoroacetic anhydride, hexafluorobutyric acid, water, sulfuric acid, supercritical carbon dioxide, acetic acid, and a combination thereof.

In an embodiment, the functionalized hydrocarbon can include methyl trifluoroacetate ester, methyl acetate, methanol, chloromethane, iodomethane, dimethylcarbonate,1,2-dichloroethane, 1,2-diiodoethane, 1,2-dichloropropane, 1,3-dichloropropane, 1,2-iodopropane, 1,3-diiodopropane ethyl trifluoroacetate ester, ethyl acetate, ethanol, ethyl chloride, ethyl iodide, ethylene glycol, ethylene esters, propyl trifluoroacetate ester, propyl acetate, propanol, propyl chloride, propyl iodide, propylene glycol, propylene esters, or a combination thereof.

In an embodiment, the amount of $A_aX_n$ and iodine-based compound that are combined with the source of functionalization can vary and can be about 0.001% to 100% as compared to the mass of the source of functionalization. In particular, the mass of the $A_aX_n$ can be about 0.14% to 10% as compared to the mass of the source of functionalization and the mass for the oxidant can be about 17%-26% as compared to the mass of the source of functionalization.

In an embodiment, $A_aX_n$ can be about 0.2 to 25 weight % or about 0.3 to 5 weight % of the first mixture. In an embodiment, the iodine-based compound can be about 2 to 40 weight % or about 5 to 25 weight % of the first mixture. In an embodiment, the source of functionalization can be about 30 to 95 weight % or about 60 to 90 weight % of the first mixture. In an embodiment, the amount of the hydrocarbon relative to the first mixture can be about 0.01 to 20 weight % or about 0.1 to 5 weight %.

In a particular embodiment, the salt ($A_aX_n$), the iodine-based compound, and the source of functionalization are disposed into a vessel to which is added a volume of methane. The purity of methane may be varied from 100% to mixtures such as that found in natural gas, crude oil, shale, and sources formed from known reported processes. The ratio of hydrocarbon relative to $A_aX_n$ can be about 1 to $1 \times 10^6$. The vessel is then pressurized with a gas sufficient to produce a pressure of about 35 to 1500 psi. The vessel is then heated to a temperature of about 100 to 235° C. for about 1 to 3 hours. Additional components of the reaction can be added intermittently to maintain production of the functionalized hydrocarbon. In addition, the mixture can be stirred during a portion or all of the time of the reaction.

In an embodiment, a combination of potassium chloride, potassium iodate, methane (800 psi) and trifluoroacetic acid are heated to about 180° C. for about three hours. The product methyl trifluoroacetate (~0.5 M) is the exclusive product with nearly 10% methane conversion. Other embodiments are described in the Examples.

In the case of utilizing water as the functionalization source, the alcohol is separated from the reaction mixture by a suitable means such as distillation. In other cases such as when the functionalization source is trifluoroacetic acid, the functionalized hydrocarbon methyl trifluoroacetate, can be separated from the reaction mixture by a suitable means such as distillation. The functionalized product, e.g., methyl trifluoroacetate is hydrolyzed to produce free alcohol and regenerate the functionalization source. Although it is understood that the process is not limited to methyl trifluoroacetate, the methyl trifluoroacetate is introduced to the hydrolysis reaction along with water in at least a stoichiometric amount to fully convert the functionalized product.

A large number of acidic and basic sources are known to promote hydrolysis. Suitable basic sources can include sodium hydroxide, potassium hydroxide, basic alumina and any combinations thereof. The preferred method of hydrolysis is acidic means as this allows for easy separation of the alcohol. Examples of acid sources can include hydrochloric acid, iodic acid, sulfuric acid, acidic alumina.

Separation of the alcohol can be accomplished though distillation, adsorption, extraction and diffusion through a membrane. Separation of the source of functionalization can be achieved by similar methods. The source of functionalization can then be recycled.

In addition to batch mode the process can be conducted in a continuous mode as follows. The hydrocarbon, salt, iodine-based compound, functionalization source, and/or pressurization gas are introduced via a liquid phase pump, compressor or solid addition mechanism to a stirred high-pressure reactor. Gas and liquids can be removed from the reactor continuously at a rate to maintain the liquid level and total pressure of the reactor. The removed gas/liquid stream can be transferred to a vessel where the gas and liquid are separated and one or both streams may be subjected to further separation or returned to the high-pressure reactor.

In certain aspects, systems and methods for hydrocarbon functionalization can comprise photolysis using a light source (hv). Without intending to be limiting, photolysis can be undertaken with light sources as described herein can be light sources such as a mercury (Hg) arc lamp or a compact fluorescent light bulb. Light sources can comprise light from the visual spectrum. In an embodiment, a light source can be a 500W compact fluorescent light bulb.

In certain aspects, systems and methods as described herein can utilize light sources for photolysis for about 24 hours to about 72 hours to produce functionalized hydrocarbons. In certain aspects, the duration of photolysis can be less than 24 hours. In certain aspects, the duration of photolysis can be more than 72 hours.

Photolytic functionalization of hydrocarbons by systems and methods as described herein can utilize one or more hydrocarbon substrates under pressure for the reaction. In an embodiment, hydrocarbons can be pressurized to a pressure of about 100 psi. In an embodiment, hydrocarbons substrates can be pressurized to a pressure of less than 100 psi. In certain aspects, hydrocarbon substrates can be pressurized to a pressure of more than 100 psi.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Potassium iodate (483 mg, 2.26 mmol), potassium chloride (25.2 mg, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) spectroscopy (FIG. 1.1), $^{13}$C NMR spectroscopy (FIG. 1.2), and gas chromatography-mass spectrometry (GC-MS) (FIG. 1.3). The percent yield was based on methyl trifluoroacetate ester product isolated divided by oxidant and methane substrate introduced into the system. The reaction yielded 97% yield based on oxidant and 24% yield based on methane.

Calculation of % yield for Example 1:

If the integral of cyclopentane is equal to 10 then it follows that:

$$\text{mmol } MeTFA = \frac{\text{integral of } MeTFA}{3} \times \text{mmol cyclopentane}$$

$$10 \ \mu L \text{ cyclopentane} = 0.107 \text{ mmol cyclopentane}$$

therefore $$\frac{61.15}{3} \times 0.107 \text{ mmol cyclopentane} = 2.18 \text{ mmol } MeTFA$$

and 2.26 mmoles KIO$_3$ and 9.78 mmol CH$_4$ used in reaction and $$\frac{2.18 \text{ mmol } MeTFA}{2.26 \text{ mmol KIO}_3} \times 100 = 97\% \text{ yield based on oxidant}$$

and $$\frac{2.18 \text{ mmol } MeTFA}{9.78 \text{ mmol CH}_4} \times 100 = 24\% \text{ yield based on methane}$$

Example 2

Calcium iodate (441 mg, 1.13 mmol), potassium iodide (56.1 mg, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) spectroscopy, $^{13}$C NMR spectroscopy, and gas chromatography-mass spectrometry (GC-MS). The percent yield was based on methyl trifluoroacetate ester product isolated divided by oxidant and methane substrate introduced into the system. The reaction yielded 6% yield based on oxidant and 1% yield based on methane.

Example 3

Ammonium iodate (436 mg, 2.26 mmol), lithium bromide (29.4 mg, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) spectroscopy, $^{13}$C NMR spectroscopy, and gas chromatography-mass spectrometry (GC-MS). The percent yield was based on methyl trifluoroacetate ester product isolated divided by oxidant and methane substrate introduced into the system. The reaction yielded 3% yield based on oxidant and 1% yield based on methane.

Example 4

Silver iodate (639 mg, 2.26 mmol), zinc chloride (46.1 mg, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) spectroscopy, $^{13}$C NMR spectroscopy, and gas chromatography-mass spectrometry (GC-MS). The percent yield was based on methyl trifluoroacetate ester product isolated divided by oxidant and methane substrate introduced into the system. The reaction yielded 22% yield based on oxidant and 1.5% yield based on methane.

Example 5

Copper (II) iodate (467 mg, 1.13 mmol), sodium chloride (4.0 mg, 0.069 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 800 psi (15.6 mmol). The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) and $^{13}$C NMR spectroscopy. The percent yield was based on methyl trifluoroacetate ester product isolated divided by oxidant and methane substrate introduced into the system. The reaction yielded 45% yield based on oxidant and 3.3% yield based on methane.

Example 6

Barium iodate (571 mg, 2.26 mmol), carbon tetrachloride (21.9 μL, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) spectroscopy, $^{13}$C NMR spectroscopy, and gas chromatography-mass spectrometry (GC-MS). The percent yield was based on methyl trifluoroacetate ester product isolated divided by oxidant and methane substrate introduced into the system. The reaction yielded 45% yield based on oxidant and 5% yield based on methane.

Example 7

Potassium iodate (483 mg, 2.26 mmol), potassium chloride (25.2 mg, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H nuclear magnetic resonance (NMR) spectroscopy, $^{13}$C NMR spectroscopy, and gas chromatography-mass spectrometry (GC-MS). The percent yield was based on methyl trifluoroacetate ester product isolated divided by oxidant and methane substrate introduced into the system. The reaction yielded 80% yield based on oxidant and 5.8% yield based on methane.

Example 8

Sodium iodate (223 mg, 1.13 mmol), sodium chloride (4.0 mg, 0.069 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with methane to 800 psi (15.6 mmol). The reactor was heated to 180° C. for 3 hours with stirring at 10 Hz. After the reactor was cooled to room temperature the gas was discharged and an internal standard of cyclopentane was added to the reaction. The liquid was analyzed by $^1$H NMR and $^{13}$C NMR spectroscopy. The percent yield was based on methyl trifluoroacetate ester product isolated divided by oxidant and methane substrate introduced into the system. The reaction yielded 59% yield based on oxidant and 4.2% yield based on methane.

Example 9

Potassium iodate (726 mg, 3.39 mmol), potassium chloride (25.2 mg, 0.338 mmol), water (2.0 mL, 111.1 mmol), and a magnetic stir bar were loaded into a glass 7 mL glass liner. The liner was placed into a custom-built 7 cm$^3$ high-pressure reactor. The reactor was assembled and pressurized with methane to 500 psi (9.78 mmol) methane and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H NMR and $^{13}$C NMR spectroscopy. The percent yield was based on methyl trifluoroacetate ester product isolated divided by oxidant and methane substrate introduced into the system. The reaction yielded 1% yield based on oxidant and 0.2% yield based on methane.

Example 10

Potassium iodate (483 mg, 3.39 mmol), potassium chloride (25.2 mg, 0.338 mmol), trifluoroacetic acid (2.0 mL, 26.1 mmol), and a magnetic stir bar were loaded into a glass 7 mL glass liner. The liner was placed into a custom-built 7 cm$^3$ high-pressure reactor. The reactor was assembled and pressurized with ethane to 340 psi (9.74 mmol) and then with argon to a total pressure of 800 psi. The reactor was heated to 180° C. for 3 hours with stirring at 10 Hz. After the reactor was cooled to room temperature the gas was discharged and an internal standard of cyclopentane was added to the reaction. The liquid was analyzed by $^1$H NMR and $^{13}$C NMR spectroscopy. The percent yield was based on methyl trifluoroacetate ester product isolated divide by oxidant and methane substrate introduced into the system. The reaction yielded 26% yield based on oxidant and 6% yield based on ethane.

Example 11

KCl (0.676 mmol), 7.7 mmol NH$_4$IO$_3$ and 8.0 mL of trifluoroacetic acid were loaded into the reactor. After the reactor was sealed, it was purged 3 times with ethane and then charged with 2070 kPa of ethane (6.7 mmol ethane). The reactor was weighed and subsequently heated and stirred for 1 hour. The reactor was removed from the heating block and cooled to room temp for 30 min. The resultant gas was collected in a gas bag and analyzed by GC-TCD. A standard of 30 mL of HOAc or methylene chloride was added to the reaction liquid. The mixture was stirred, then a sample was removed for analysis. The products were analyzed by $^1$H NMR and GC-MS. 2.03 mmol EtTFA; 0.13 mmol EtCl and 0.06 mmol 1,2-bis(trifluoroacetyl)ethane (glycol) were formed in the reaction.

Example 12

KCl (0.676 mmol), 7.7 mmol NH$_4$IO$_3$ and 8.0 mL of trifluoroacetic acid were loaded into the reactor. After the reactor was sealed, it was purged 3 times with propane and finally charged with 830 kPa propane (3.0 mmol propane). The reactor was weighed and subsequently heated and stirred for 2 h. The reactor was removed from the heating block, cooled to room temp. The resultant gas was collected in a gas bag and analyzed by GC-TCD. A standard of 30 mL of HOAc was added to the reaction liquid. The mixture was stirred, after which a sample was removed for analysis. The products were analyzed indentified by $^1$H NMR and GC-MS. 121 mmol of 1-trifluoroacetopropane, 404 mmol of 2-trifluoroacetopropane and 236 mmol of bis(1,2-trifluoroaceto)propane were formed in the reaction.

Example 13

Methane, a stir bar, 0.676 mmol KCl, 7.7 mmol NH$_4$(IO$_3$) and 8.0 mL of trifluoroacetic acid were loaded into the 16.1 mL VCO reactor that contained a tight fitting Teflon liner. After the reactor was sealed and weighed, it was purged three times with CH$_4$/Ne. The reactor was pressurized to 340 kPa O$_2$ (0.8 mmol O$_2$) and finally pressurized to 3450 kPa of 90 mol % CH$_4$/10 mol % Ne (7.6 mmol CH$_4$). The reactor was subsequently heated and stirred (800 rpm) for 1 hour. The reactor was removed from the heating block, placed in front of a fan and cooled to room temp for 30 min. The resultant gas was collected in a gas bag and analyzed by GC-TCD. A standard of 30 mL of HOAc and/or 30 mL of methylene chloride was added to the reaction liquid. The mixture was stirred, then a sample was removed for analysis. The products were analyzed by $^1$H NMR, $^{13}$C NMR and GC-MS. 1.73 mmol MeTFA and 0.06 mmol of MeCl were formed. The reaction with ethane and oxygen were charged first with 255 kPa O$_2$ then filled to a final pressure of 2070 kPa with ethane. The reaction was then carried out as described above.

Example 14

Potassium periodate (1.77 g, 7.7 mmol), potassium chloride (50 mg, 0.67 mmol), trifluoroacetic acid (8.0 mL, 104.4 mmol), and a magnetic stir bar were loaded into a 12 mL teflon liner. The liner was placed into a custom-built 16 cm$^3$ high-pressure reactor. The reactor was assembled and three times purged with CH$_4$/Ne (9:1) to 500 psi, then filled with a total pressure of 500 psi. The reactor was heated to 200° C. for 1 hour with stirring at 10 Hz. After the reactor was cooled to room temperature, the gas was discharged and an internal standard of 1,2-dichloroethane or dichloromethane was added to the reaction. The liquid was analyzed by $^1$H nuclear magnetic resonance (NMR) spectroscopy (FIG. 3.1) and gas chromatography (with flame ionization detector) spectrometry (GC-FID). The reaction yielded 1.7 mmol of methyl trifluoroacetate.

Example 15

Potassium periodate (115 mg, 0.5 mmol), potassium chloride (6 mg, 0.08 mmol), trifluoroacetic acid (2.5 mL, 32.6 mmol), and a magnetic stir bar were loaded into a custom-built 7 cm$^3$ high-pressure reactor. The reactor was assembled and three times purged with CH$_4$/Ne (9:1) to 500 psi, then filled with a total pressure of 500 psi. The reactor was heated to 150° C. for 2 hours with stirring at 10 Hz. After the reactor was cooled to room temperature the gas was discharged and an internal standard of 1,2-dichloroethane was added to the reaction. The liquid was analyzed by $^1$H nuclear magnetic resonance (NMR) spectroscopy and gas chromatography (with flame ionization detector) spectrometry (GC-FID). The reaction yielded 0.18 mmol of methyl trifluoroacetate.

Example 16

An 8 mL microwave vial equipped with a stirbar was charged with norbornane (2.5 mmol), orthoperiodic acid (0.25 mmol), TFA (4 mL), and trifluoroacetic anhydride (4.2 mmol). The vial was then crimped shut and heated to 60° C. for 18 h with vigorous stirring. The entire reaction was added to 4 mL of chloroform. Dodecane (0.25 mmol) was added as an internal standard. The reaction was then extracted with water (3×5 mL) and the organic washings dried over MgSO$_4$. The reaction was analyzed via GC-MS relative to the internal standard yielding norbornyl trifluoroacetate in 208±4% yield (n=3) relative to the amount of iodine(VII). Addition of potassium chloride in a separate run gave similar yields (~200%) yet required much shorter reaction times (3 h). FIG. 4.1 is a scheme illustrating the oxidation of norbornane using H$_5$IO$_6$ as the oxidant with catalytic KCl.

Example 17

An 8 mL microwave vial equipped with a stirbar was charged with adamantane (1.0 mmol), ammonium periodate (1.0 mmol), and KCl (0.15 mmol). TFA (4 mL) was added and the vial sealed with a crimp cap. The mixture was then stirred at 60 C for 1 hour at which point the vial was allowed to cool. The entire reaction was added to 4 mL of chloroform. Dodecane (1.0 mmol) was added as an internal standard. The reaction was then extracted with water (3×5 mL) and the organic washings dried over MgSO$_4$. The reaction was analyzed via GC-MS relative to the internal standard yielding 1-adamantyl trifluoroacetate in 58±2% yield, based on starting adamantane, as the only product. The control reaction without chloride showed only trace amounts of product. FIG. 5.1 is a scheme that illustrates the oxidation of adamantane using ammonium periodate and catalytic potassium chloride.

Introduction:

Natural gas is a chemical feedstock and a primary fuel that accounts for nearly 25% of the world's energy.[1] A significant amount of natural gas is "stranded". However, the expense of infrastructure associated with pipelines or liquefaction often make transportation uneconomical.[2] The Global Gas Flaring Reduction Partnership estimates that 140 billion cubic meters of natural gas are flared or vented annually.[3] New gas to liquid (GTL) technologies that efficiently convert alkanes from natural gas into easily transportable liquids would allow utilization of this vast hydrocarbon resource.

New chemistry is needed for the direct conversion of gaseous alkanes to liquid alcohols.[4] The conversion of alkanes and oxygen to alcohols is thermodynamically favorable (by ~30 kcal/mol for methane/½O$_2$ to methanol), but the large activation barriers associated with breaking strong (~100-105 kcal/mol)[5] non-polar C—H bonds of alkanes and relatively lower barriers for reaction of the alcohol products make direct conversion difficult.[6] As a result, even modern methods for alkane functionalization involve indirect and energy-intensive processes. For example, the conversion of methane to methanol by current technologies requires methane reforming to generate a mixture of carbon monoxide and dihydrogen (syngas) followed by conversion of syngas to methanol. The ethane, propane and butane portions of natural gas can be converted to olefins by high temperature (~850° C.) cracking. Reactions that could enable the direct conversion of alkanes from natural gas to partially oxidized products under more moderate conditions have been highly sought.[6-11] In particular, the preparation of mono-functionalized species (RX) at temperatures ≤250° C. and pressures ≤3500 kPa would allow less energy intensive and capital intensive GTL conversions. Radical-based chemistry provides a platform to cleave strong alkane C—H bonds; however, the oxidized products are typically more reactive than the starting alkane.[6] Accordingly, over oxidation has been an issue for catalytic oxychlorination reactions,[12-16] which involve passing mixtures of CH$_4$, HCl and O$_2$ over a catalyst bed at temperatures >350° C.[17,18] The direct use of halogens to produce MeX has also been developed.[19-22]

Another option for direct alkane partial oxidation is based on the use of transition metals. Biomimetic approaches for C—H functionalization using high valent oxo complexes have been reported.[23-30] Another method is the use of transition metals that directly coordinate and activate C—H bonds.[7,8,31-36] This strategy has been used to functionalize alkanes by metal-mediated alkane dehydrogenation.[37-42] Also, electrophilic late transition metal complexes (e.g., Pt, Pd, Hg and Au) have been shown to catalyze methane functionalization in super acidic media.[43-47] Product inhibition and product separation turned out to be significant challenges for these processes. The use of main group metals for alkane functionalization that do not require super acids has been reported recently.[48] Metal-mediated transformations that likely involve radicals have also been reported.[49-51] In an alternative approach, Ag complexes catalyze conversions of alkanes to esters using ethyl diazoacetate.[52,53]

Hypervalent iodine species[54-56] are also capable of functionalizing non-polar C—H bonds through electrophilic, non-radical pathways.[21,22,57-60] I$_2$[61-64] and KIO$_3$[64] convert methane to MeOSO$_3$H in the super acidic medium H$_2$SO$_4$ and SO$_3$ (oleum).[63] Other halogen-based systems (e.g., I(TFA)$_3$)[44] have been demonstrated to functionalize hydrocarbons with low selectivity to esters.[17,45,46,63] An efficient process for alkane C—H oxygenation has remained an elusive goal. We describe here a selective reaction of methane and higher alkanes with hypervalent iodine species mediated by catalytic quantities of chloride in weaker acid media such as HTFA, aqueous HTFA, acetic acid and water.

Results and Discussion:

We have identified a hypervalent iodine-based system that effectively and selectively oxidizes methane, ethane and propane in non-super acid media to the corresponding alcohol esters (eq 1). The reactions occur with selectivity for mono-functionalized product. Methane is converted over a broad range of pressures (240-6900 kPa) and at temperatures ≤235 OC. Significantly, the system requires sub-stoichiometric amounts of chloride to generate the active species that reacts with the alkanes. In the absence of chloride the reaction is inefficient and/or unselective. The iodate/chloride system is much more efficient than the hypervalent iodine systems without chloride such as I$_2$, iodate or I(TFA)$_3$. This suggests that the iodate/chloride process functions via a different mechanism than these systems (see below).

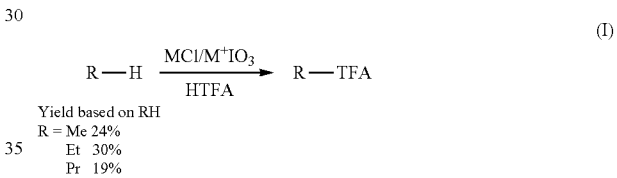

(1)

Yield based on RH
R = Me 24%
Et 30%
Pr 19%

Pressurizing a mixture of KCl (0.676 mmol) and NH$_4$IO$_3$ (7.70 mmol) in HTFA to 3450 kPa with methane (8.4 mmol) and heating at 180° C. for 1 h, results in the formation of 1.81 mmol of MeX (X=TFA or Cl) in about 20% yield (eq 2). Yields are based on total methane present as determined by weighing reactors before and after methane addition. The presence of chloride is essential to the reaction (see below), and the use of sub-stoichiometric quantities (based on iodate or methane converted) suggests that chloride might play a catalytic role.

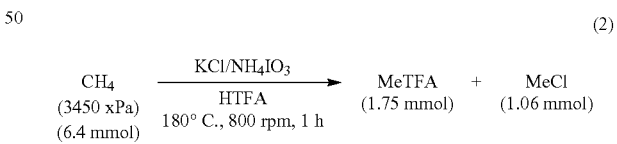

(2)

MeTFA was found to be relatively stable under the reaction conditions. In reactions where 0.90 mmol $^{13}$C-MeTFA, 0.676 mmol KCl and 7.70 mmol NH$_4$IO$_3$ were added to 8.0 mL of HTFA with 3450 kPa of methane and heated for 1 h at 180° C., only 0.14 mmol (15% of starting material) of $^{13}$C-MeTFA was consumed (FIG. 2.1). GC-MS data showed that the $^{13}$MeTFA was transformed to $^{13}$CO$_2$. No evidence of $^{13}$CH$_2$X$_2$ Or $^{13}$CHX$_3$ intermediates was observed by $^1$H NMR. In contrast, 1.81 mmol of MeTFA were produced from CH$_4$ during this same time period. This result highlights the "protecting" ability of the electronwithdrawing TFA moiety towards over oxidation. A detailed kinetic comparison of the reactivity of CH$_4$ and MeTFA is not possible since the concentration of CH$_4$ under these conditions is not known.

Carbon dioxide (observed by GC-TCD) is formed during the course of the reaction. To determine the source of carbon dioxide (methane or HTFA) the functionalization of $^{13}$CH$_4$ was carried out. Reactions charged with 240 kPa (0.652 mmol) $^{13}$CH$_4$ converted ~15% of the $^{13}$CH$_4$ with 91% selectivity for $^{13}$CH$_3$X (X=CO$_2$CF$_3$, Cl) (eq 3). Products were confirmed through analysis of the resulting liquid and headspace by $^1$H NMR and $^{13}$C NMR spectroscopy (see FIG. 2.2) and GC-MS (see Supporting Information). GC-MS of the products from the $^{13}$C labeled methane reaction demonstrated that <2% of the methane was over oxidized to CO$_2$ (presumably, the remaining CO$_2$ originates from decarboxylation of HTFA as this is the only other carbon source in the reaction). Mass balance of the resultant mixture of methane, MeTFA, CH$_3$Cl, CH$_2$Cl$_2$ and CO$_2$ accounted for ~99% of the initial methane (see Supporting Information).

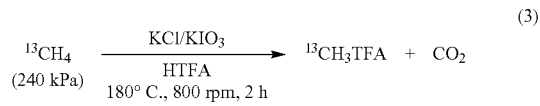

(3)

The influence of methane pressure on conversion efficiency was probed. Although the iodate/chloride system is effective at lower pressures (<3450 kPa), yields of MeTFA after 2 h are higher at elevated pressures (≥3450 kPa) of methane. Analyzing reactions between 240 and 5520 kPa after 2 h of reaction at 180° C. revealed that increasing methane pressure provides increased production of the methyl ester (FIG. 2.3). Although conditions of the reaction make a rigorous kinetic analysis difficult, the data in FIG. 2.3 are consistent with a reaction that is first order in methane assuming that Henry's Law is followed. At 6900 kPa after 2 h of reaction, the production of MeTFA was observed to reach a maximum value of ~0.5 M MeTFA with 130:1 ratio of MeTFA:CH$_3$Cl. For each reaction, sampling of the reactor headspace and analysis by GC-TCD reveals negligible or no CH$_3$Cl.

The partial oxidation of methane can also be achieved over a wide temperature range, between 100-235° C. (FIG. 2.4). Reactions at 235° C. with 3450 kPa of methane, 0.676 mmol of KCl, 7.70 mmol of NH$_4$IO$_3$ are rapid with ~24% conversion of methane to MeTFA in 20 min.

Both chloride and iodate were observed to play a crucial role in the methane conversion (see Supporting Information). MeTFA is not formed in substantial amounts in the absence of a chloride source (<1% conversion for "background" reactions that use iodate in the absence of chloride), and use of other halogens (F$^-$, Br$^-$ or I$^-$) gives only background reactions.

Exclusion of iodate results in no reaction. The use of KBrO$_3$ gives only small amounts of MeTFA while a complex mixture of intractable products was observed for reactions using KClO$_3$ as an oxidant. Methane conversions varied with the choice of chloride and iodate sources (FIG. 2.5). Potassium chloride was found to be the optimal source of chloride. Other chloride sources, including metallic and non-metallic sources, were found to successfully convert methane to methyl trifluoroacetate (FIG. 2.5). Of the iodate sources tested, only iodic acid and silver iodate showed poor activity. Ammonium iodate surpassed other iodates by a factor of nearly two. $^1$H NMR spectroscopy indicated that the ammonium ion is not consumed during the course of the methane functionalization reaction. The effect of the potassium chloride concentration was examined (Table 1). Only 0.02 mmol of MeTFA formed without the addition of KCl due to the background reaction. As the amount of KCl is increased, the yield of MeTFA increases. High yields of MeTFA were determined for the addition of 451 mmol, 676 mmol and 901 mmol of KCl. Also, the amount of MeCl increases with increased amount of KCl.

TABLE 1

Impact of KCl concentration on methane conversion to MeX.

| KCl (μmol) | MeTFA (mmol) | MeCl (mmol) |
|---|---|---|
| 0 | 0.02 | Not observed |
| 225 | 0.11 | Not observed |
| 451 | 1.26 | 0.03 |
| 676 | 1.75 | 0.06 |
| 901 | 2.00 | 0.06 |

Conditions: 7.7 mmol NH$_4$IO$_3$, 8.0 mL HTFA, p$_{CH4/Ne}$ = 3450 kPa, 180° C., 1 h; 600 rpm.

The results of acid screening are shown in Table 2. Trifluoroacetic acid was observed to give the highest yields of the methyl ester. In contrast to chemistry that was developed around elemental iodine,[61-64] only trace amounts of functionalized products were observed in sulfuric acid when using IO$_3^-$/Cl$^-$. Electrophilic functionalization of alkanes in acids weaker than H$_2$SO$_4$ and HTFA can be a challenge, but the IO$_3^-$/Cl$^-$ system can be performed in aqueous HTFA or even acetic acid. For example, reaction in acetic acid led to the formation of 0.20 mmol of methyl acetate (MeOAc) after 2 h at 180° C. Furthermore, reactions using 6.5 mL of a 1:3 mol % H$_2$O:HTFA mixture containing 0.676 mmol KCl, 7.7 mmol NH$_4$IO$_3$ and 3450 kPa (8.4 mmol) of methane heated at 180° C. for 1 h resulted in the formation of 1.21 mmol MeTFA, 0.03 mmol MeCl and 0.004 μmol of MeOH.

Ethane was found to react with even greater conversion and selectivity than methane (eq 4). Solutions of KCl (0.676 mmol) with NH$_4$IO$_3$ (7.7 mmol) in 8.0 mL HTFA placed under 2070 kPa C$_2$H$_6$ (6.7 mmol) lead to the formation of 2.03 mmol of mono-functionalized EtTFA (30% yield based on ethane) with a small amount of 1,2-di-functionalized product (0.06 mmol) in 1 h at 180° C. The resulting $^1$H NMR spectrum is shown in FIG. 2.6. The selectivity for EtX (X=TFA, Cl) products was found to be ~97%. In an independent reaction, ethylene was converted in ~50% yield to ethylene glycol bistrifluoroacetate under the catalytic conditions with no observed 1,1-bis-TFA product. Under identical conditions in the absence of KCl only 1% of the ethane was functionalized to EtTFA. The reaction of propane (830 kPa, 3.0 mmol) with 0.676 mmol KCl and 7.7 mmol NH$_4$IO$_3$ in HTFA at 180° C. resulted in the production of 1-propyl (0.121 mmol), 2-propyl (0.202 mmol) and 1,2-propyl (0.236 mmol) trifluoroacetate products as shown in eq 5 corresponding to 19% conversion based on propane. The reaction is 58% selective for mono-functionalized products that were formed in a nearly 1:2 ratio of terminal to internal oxidation. The production of any terminal functionalized propane is rare. For example, I(III)-mediated oxidation of hexane has been reported to oxidize only the internal methylene groups.[57,58]

TABLE 2

Comparison of solvents for methane conversion to MeX.

| Entry | Solvent | Product | Yield (mmol) |
|---|---|---|---|
| 1 | $CF_3CO_2H$ | $MeO_2CCF_3$ | 0.42 |
| 2 | $CF_3(CF_2)_2CO_2H$ | $MeO_2C(CF_2)_2CF_3$ | 0.38 |
| 3 | $CH_3CO_2H$ | $MeO_2CCH_3$ | 0.20 |
| 4 | $H_2SO_4$ | $MeOSO_3H$ | trace |
| 5 | $H_2O$ | MeOH | trace |

Conditions: 0.338 mmol [Cl⁻][ 2.26 mmol $NH_4IO_3$; 2.0 mL solvent; $p_{CH4/Ne}$ = 5520 kPa; 180° C.; 2 h; 600 rpm.

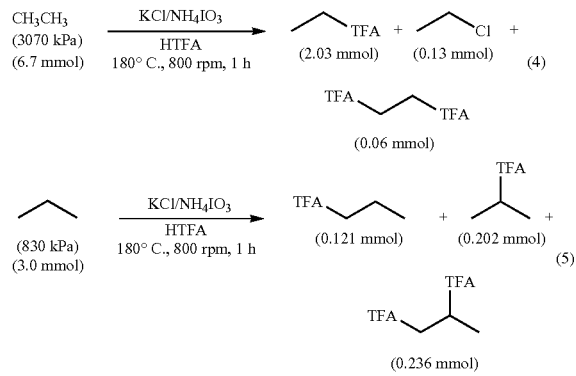

Other iodine reagents proved feasible for alkane conversion (Table 3). Species of interest include ICl, $ICl_3$, $(TFA)_3$, $IO^+$ and $IO_2^+$.

TABLE 3

Stoichiometric partial oxidation of methane using various iodine sources.

| Entry | Species | Additive | % Yield[a] MeTFA |
|---|---|---|---|
| 1 | $I_2$ | — | — |
| 2 | $I_2$ | KCl | — |
| 3 | $I_2$ | $NH_4IO_3$ | 2 |
| 4 | ICl | — | — |
| 5 | $ICl_3$ | — | 5 (43)[b] |
| 6 | $I(TFA)_3$ | — | 7 |
| 7 | $I(TFA)_3$ | KCl | 43 |
| 8 | $I_2O_4$ | — | 2 (15)[c] |
| 9 | $I_2O_4$ | KCl | 30 (17)[c] |
| 10 | $I_2O_5$ | — | 1 (2)[b] |
| 11 | $I_2O_5$ | KCl | 4.1 |
| 12 | $(IO_2)_2S_2O_7$ | — | <1 |
| 13 | $(IO_2)_2S_2O_7$ | KCl | 48 |
| 14 | $(IO)_2SO_4$ | — | 5.3 |
| 15 | $(IO)_2SO_4$ | KCl | 31 |

[a] % yield based on moles iodine reagent.
[b] % yield MeCl given in parenthesis.
[c] % yield MeI given in parenthesis.
Conditions: 0.4 mmol iodine reagent; 0.1 mmol KCl if added; $p_{CH4/Ne}$ = 3450 kPa, 180° C., 800 rpm; 1 h.

The reaction of $CH_4$ in HTFA at 180° C. with 0.4 mmol $I(TFA)_3$, $I_2O_4$,[69] $I_2O_5$,[41] $[(IO_2)_2S_2O_7]$[70] or $[(IO)_2SO_4]$[71] in the absence of chloride results in minimal conversion (≤7% yield) to MeTFA (Table 3). But, for all these iodine-based reagents except $I_2O_5$, the addition of 0.1 mmol KCl results in a dramatic increase in the yield of MeTFA (Table 3). Similar to the iodate/chloride reactions, KCl is effective in a sub-stoichiometric quantity. The highest percent yield of MeTFA was achieved using $[(IO_2)_2S_2O_7]$, which gave a nearly 50% yield. $I(TFA)_3$ with KCl also gave a high yield (43%) of MeTFA, and the combined yield of MeTFA and MeI (47%) was high for $I_2O_4$ and KCl.

SUMMARY

Alkanes are converted to mono-functionalized esters in good yields with the use of simple chloride salts (in catalytic amounts) and with iodate as the sole oxidant in acidic media such as trifluoroacetic acid, acetic acid or even aqueous trifluoroacetic acid. The system operates over a large range of pressures (240-6900 kPa) and temperatures (100-235° C.) and exhibits excellent selectivity for monofunctionalized products. Conversions of methane to MeTFA>20% have been achieved, and conversion of ethane is even more efficient with ~30% yield of EtTFA. Although propane conversion is less efficient, the ability to form mono-functionalized products selectively with some terminal activation is notable. These values for alkane conversion meet many of the established benchmarks for efficient alkane functionalization.[72] A potential benefit of the iodate/chloride system is that iodine (the byproduct of $KCl/IO_3^-$ oxidation reactions) can be reoxidized to iodate in basic aqueous solution with molecular oxygen. Also, iodates have been generated from iodide sources electrochemically.[73] The distinct reactivity imparted by chloride (compared with $I_2$, $IO_3^-$, $I(TFA)_3$, etc. with no chloride or these species with other halides) is unique and without precedent, resulting in substantial increases in efficiency for production of mono-functionalized alkanes. The exact role of chloride is unknown at this point and will be the subject of future studies, but the chloride enhancement is observed for several iodine-based reagents (Table 3). Given the differences between classic oxychlorination and the iodate/chloride process (e.g., reaction temperature, product selectivity and efficacy for ethane and propane), it seems unlikely that the formation of chlorine radical is the key role of chloride. It is possible that chloride bonds with the active iodine-based reagent to provide an electronic modulation for the C—H bond breaking step and/or the C—O bond-forming step. Iodosyl chloride and iodyl chloride have been observed experimentally.[74] The presence of iodine-oxo bonds suggests a possible similarity to C—H bond breaking by metal oxo or imide complexes.[23,75-77] But, the enhancement observed when adding chloride to the $I(TFA)_3$ reaction suggests that the chloride enhancement is not limited to iodine oxides. Although challenges remain, the reported iodate/chloride process functionalizes alkanes rapidly (in 20 min under some conditions), with good conversion and selectivity, under a broad range of temperatures and pressures and with an oxidant that in theory can be thermally recycled using dioxygen.

Experimental Section

General Considerations:

Unless stated otherwise, all reactions were prepared in air. Trifluoroacetic acid (HTFA), trifluoroacetic anhydride (TFAA), methyl trifluoroacetate ester (MeTFA), acetic acid (HOAc), iodic acid, formic acid, sulfuric acid, iodine trichloride, iodine monochloride, $I_2O_5$, iodomethane, chloromethane, iodine as well as all iodates and chlorides were purchased from VWR and used as received. Methane/neon (9:1 mol), ethane and propane were purchased from GTS Welco. Trifluoroacetic acid-$d_1$ (DTFA), $^{13}$C-methane and $^{13}$C-methanol were purchased from Cambridge Isotopes and used as received. Iodyl pyrosulfate,[70] iodosyl sulfate,[71] diiodine tetraoxide[69] and tris-(trifluoroaceto) iodine[80] were prepared according to literature procedures. $^1$H and $^{13}$C NMR spectra were recorded on either a Bruker 600, 500 or 300 MHz NMR spectrometer. NMR spectra taken in HTFA or DTFA included a capillary tube filled with $C_6D_6$ that was used as an internal lock reference. Chemical shifts in HTFA are reported relative to standards of HOAc ($^1$H NMR d=2.04) or dichloromethane (DCM; $^1$H NMR d=5.03). This shift was chosen so that the products would remain at the same chemical shifts when using different standards. At least one reaction was spiked with the alternative internal standard to ensure the integrity of the standards and to ensure that the standard was not a product of the reaction (i.e., DCM was used to determine if HOAc was a product of the reaction). GC-MS were obtained on a Shimadzu GC-2010 equipped with a Restek RT®-Qbond 30 m×8 mm fused silica PLOT column. GC-TCD were obtained with a Shimadzu GC-2014 equipped with a 500 mL injection loop in which the sample passed through 3 columns in series (Hayesep® T 80/100 mesh 0.5 m×2.0 mm, Supelco® 60/80 Mesh 5 Å molecular sieve 2.0 m×2.1 mm and Hayesep® Q 80/100 mesh 1.5 m×2.0 mm). UV-Vis spectra were recorded on Varian Carey 300 Bio UV-Vis spectrophotometer. Reactions of $Cl^-/IO_3^-$ in acid with alkanes:

Reactions were carried out in two separate types of high-pressure reactors. Reactions consisting of a solvent volume of >2.0 mL used in-house built high-pressure reactors constructed primarily of stainless steel Swagelok® parts. The reactors were equipped with Teflon liners. With liners inserted, the average reactor volume is 16.1 mL. Heating was accomplished through inductive heat transfer from tight fitting custom aluminum blocks. Screening of reagents and conditions were typically carried out in a custom built Asynt Ltd. high-pressure carousel. The carousel is constructed of Hastelloy® C-276 and contains 9×7 mL reaction chambers. Reactions were carried out in glass liners within the reaction chambers. Reaction temperatures were maintained through direct heat from a RTC-basic hotplate equipped with temperature control. The carousel was insulated by wrapping in fiberglass fabric. The amounts reported for products formed for all functionalization reactions are the average of at least 3 independent reactions.

Methane Functionalization:

In a typical reaction with methane, a stir bar, 0.676 mmol KCl, 7.7 mmol $NH_4(IO_3)$ and 8.0 mL of HTFA were loaded into the 16.1 mL VCO reactor that contained a tight fitting Teflon liner. After the reactor was sealed and weighed, it was purged three times with $CH_4$/Ne and finally charged with 3450 kPa of 90 mol % $CH_4$/10 mol % Ne (8.4 mmol $CH_4$). The reactor was weighed to quantify the amount of gas added, then subsequently heated and stirred (800 rpm) for 1 h. The reactor was removed from the heating block, placed in front of a fan and cooled to room temp for 30 min. The reactor was reweighed to ensure no leakage occurred over the course of the reaction. The resultant gas was collected in a gas bag and analyzed by GC-TCD. A standard of 30 mL of HOAc and/or 30 mL of DCM was added to the reaction liquid. The mixture was stirred, then a sample was removed for centrifugation. The products were analyzed by $^1$H NMR, $^{13}$C NMR and GC-MS. 1.75 mmol MeTFA and 0.06 mmol of MeCl were formed. $^1$H NMR (d)=3.85 (3H, $H_3C-O_2CCF_3$, s); $^{13}$C NMR (d)=50.8 ($H_3C-O_2CCF_3$, q, $^4J_{C-F}$=17 Hz), carbonyl carbon and $CF_3$ carbon overlap with HTFA resonances.

In a typical reaction with methane in the carousel, a stir bar, 0.338 mmol KCl, 2.26 mmol $NH_4(IO_3)$ and 2.0 mL of HTFA were loaded into individual glass vials. The vials were transferred into the reactor. After the reactor was sealed, it was purged 3 times with $CH_4$/Ne and finally charged with 5515 kPa of 90 mol % $CH_4$/10 mol % Ne. The reactor was subsequently heated and stirred (600 rpm) for 2 h. The reactor was removed from the heating block, placed in front of a fan and cooled to room temp for 30 min. The resultant gas was collected in a calibrated gas burette to obtain the final amount of gas contained in the reactor. This gas was analyzed by GC-TCD. A standard of 10 mL of HOAc and/or 10 mL of DCM was added to the reaction liquid. The mixture was stirred, then a sample was removed for centrifugation. The products were analyzed by $^1$H NMR spectroscopy, $^{13}$C NMR spectroscopy and GC-MS. The amount of MeTFA formed (minus background; 0.04 mmol) was determined to be 0.86 mmol MeTFA.

$^{13}$C-Methane Functionalization:

Four carousel chambers were individually charged with a stir bar, 0.338 mmol KCl, 2.26 mmol $KIO_3$ and 2.0 mL of HTFA. After the reactor was sealed, it was purged 2 times with argon, once with $^{13}CH_4$ and finally charged with 240 kPa of $^{13}CH_4$ (0.652 mmol). The reaction was heated for 2 h and stirred at 600 rpm. The reactor was cooled to room temperature over 30 min. The resultant gas was collected in a gas bag. A portion was evaluated by GC-MS to determine the amount of $^{13}CO_2$ produced (0.011 mmol), and the remaining was vented directly into the sample loop of the GC-TCD and final gas concentrations were determined through independently determined calibration curves. A standard of 10 mL of HOAc was added to the reaction liquid. The mixture was stirred, and a sample was removed for centrifugation. The products were analyzed by $^1$H NMR spectroscopy, $^{13}$C NMR spectroscopy and GC-MS. From the reaction 80 mmol of $^{13}CH_3TFA$, 6 mmol of $^{13}CH_3Cl$ and 5 mmol of $^{13}CH_2Cl_2$ were formed. $^1$H NMR (d)=3.85 (3H, $^{13}CH_3TFA$, d, $^1J_{C-H}$=151 Hz), 2.78 (3H, $^{13}CH_3Cl$, d, $^1J_{C-H}$=150 Hz), 5.03 (2H, $^{13}CH_2Cl_2$, d, $^1J_{C-H}$=178 Hz). $^{13}$C NMR (d)=50.8 ($^{13}CH_3TFA$), 25.1 ($^{13}CH_3Cl$), 53.0 ($^{13}CH_2Cl_2$).

Retention of MeTFA:

In a vial, 1.0 g of $^{13}CH_3OH$ was added slowly to an equimolar amount of TFAA during continuous stirring to produce $^{13}CH_3$-TFA and HTFA. A known volume was sampled and diluted into HTFA. The sample was spiked with HOAc and $^1$H NMR was used to determine the concentration of $^{13}CH_3$-TFA. A reaction was then set up analogous to the methane functionalization reaction in the 16.1 mL VCO reactor described above (0.667 mmol KCl; 7.7 mmol $NH_4IO_3$; 8.0 mL HTFA). This mixture was then spiked with 0.9 mmol of the $^{13}CH_3$-TFA stock solution. The reactor was sealed, purged with $CH_4$ 3x times and pressurized to 3450 kPa of $CH_4$/Ne (9:1). The reaction was heated (180° C.) and stirred (800 rpm) for 1 h, and cooled to room temperature. The over pressure was vented into a gas bag and this gas was analyzed by GC-MS. 30 mL of HOAc was added as a standard and the reaction was stirred and sampled as detailed above. $^1$H NMR of the liquid revealed that 85% of the $^{13}CH_3$-TFA was retained and that 1.7 mmol MeTFA was formed during the reaction. The presence of methane was found to not be crucial to the reaction as a similar reaction run without the overpressure of methane resulted in the same amount of $^{13}CH_3$-TFA retained.

Functionalization Reactions of $CH_4$ and $C_2H_6$ with Added $O_2$:

In a typical reaction with methane, a stir bar, 0.676 mmol KCl, 7.7 mmol $NH_4(IO_3)$ and 8.0 mL of HTFA were loaded into the 16.1 mL VCO reactor that contained a tight fitting Teflon liner. After the reactor was sealed and weighed, it was purged three times with $CH_4$/Ne. The reaction was pressurized to 340 kPa $O_2$ (0.8 mmol $O_2$) and finally pressurized to 3450 kPa of 90 mol % $CH_4$/10 mol % Ne (7.6 mmol $CH_4$). The reactor was subsequently heated and stirred (800 rpm) for 1 h. The reactor was removed from the heating block, placed in front of a fan and cooled to room temp for 30 min. The resultant gas was collected in a gas bag and analyzed by GC-TCD. A standard of 30 mL of HOAc and/or 30 mL of DCM was added to the reaction liquid. The mixture was stirred, then a sample was removed for centrifugation. The products were analyzed by $^1H$ NMR, $^{13}C$ NMR and GC-MS. 1.73 mmol MeTFA and 0.06 mmol of MeCl were formed. The reaction with ethane and oxygen were charged first with 255 kPa $O_2$ then filled to a final pressure of 2070 kPa with ethane. The reaction was then carried out as described above.

Methane Functionalization with Various Sources of Iodine:

Reactions in this case were carried out with various sources of iodine in different oxidation states. These reactions were carried out with and without added potassium chloride. The reactions using ICl and $ICl_3$ were prepared inside a glovebox. A typical reaction is as follows: A stir bar, 0.4 mmol $I_2O_4$, 0.1 mmol KCl and 6.0 mL of HTFA were loaded into the 16.1 mL VCO reactor which contained a tight fitting Teflon liner. The reactors were sealed and weighed. The reactor was attached to a high-pressure line and flushed 3x with $CH_4$/Ne (9:1). The reactor was then charged to 3450 kPa (8.4 mmol $CH_4$) with the same gas mixture and weighed again to obtain the amount of gas added. The reactor was weighed and subsequently heated and stirred (800 rpm) for 1 h. The reactor was removed from the heating block, placed in front of a fan and cooled to room temp for 30 min. The resultant gas was collected in a gas bag and analyzed by GC-TCD. A standard of 30 mL of HOAc and/or 30 mL of DCM was added to the reaction liquid. The mixture was stirred, then a sample was removed for centrifugation. The products were analyzed by $^1H$ NMR, GC-MS. 0.238 mmol MeTFA and 0.137 mmol of MeCl were formed. Yields for these reactions are given in terms of moles of iodine reagent. For this reaction the yield for MeTFA is given as 30% and for MeCl as 17%.

Methane Functionalization with $SO_2Cl_2$ or N-Chlorosuccinimide: The reactions were performed according to the methane functionalization procedure above, except $SO_2Cl_2$ or N-chlorosuccinimide (NCS) was used instead of KCl. For the reactions, 0.676 mmol NCS or 0.338 mmol $SO_2Cl_2$ were combined with 7.7 mmol $NH_4IO_3$ in 8 mL of HTFA and pressurized with 3450 kPa $CH_4$. The reactors were heated at 180° C. for 1 h, then cooled and analyzed.

Ethane Functionalization:

In a typical reaction with ethane a stir bar, 0.676 mmol KCl, 7.7 mmol $NH_4IO_3$ and 8.0 mL of HTFA were loaded into the reactor. After the reactor was sealed, it was purged 3 times with ethane and finally charged with 2070 kPa of ethane (6.7 mmol ethane). The reactor was weighed and subsequently heated and stirred (800 rpm) for 1 h. The reactor was removed from the heating block and cooled to room temp for 30 min. The resultant gas was collected in a gas bag and analyzed by GC-TCD. A standard of 30 mL of HOAc or DCM was added to the reaction liquid. The mixture was stirred, then a sample was removed for centrifugation. The products were analyzed by $^1H$ NMR and GC-MS. 2.03 mmol EtTFA; 0.13 mmol EtCl and 0.06 mmol 1,2-bis(trifluoroacetyl)ethane (glycol) were formed in the reaction. $^1H$ NMR (d)=1,2-bis(trifluoroacetyl)ethane—4.49 (4H, 4.25, $H_2C$—$O_2CCF_3$). ethyl trifluoroacetate: 4.27 (2H, $CH_3H_2C$—$O_2CCF_3$, q, $^3J_{H-H}$=7 Hz), 1.18 (3H, $CH_3H_2C$— $O_2CCF_3$, t, $^3J_{H-H}$=7 Hz). ethyl chloride—4.19 ($CH_3CH_2Cl$, br), 2.08 ($CH_3CH_2Cl$, overlap with HOAc standard).

Ethylene Functionalization:

In a typical reaction with ethylene a stir bar, 0.676 mmol KCl, 7.7 mmol $NH_4IO_3$ and 8.0 mL of HTFA were loaded into the reactor. After the reactor was sealed, it was purged three times with ethylene and finally charged with 1379 kPa ethylene (4.3 mmol ethylene). The reactor was weighed and subsequently heated and stirred (800 rpm) for 1 h. The reactor was removed from the heating block and cooled to room temp for 30 min. The resultant gas was collected in a gas bag and analyzed by GC-TCD. A standard of 30 mL of DCM was added to the reaction liquid. The mixture was stirred, then a sample was removed for centrifugation. The products were analyzed by $^1H$ NMR spectroscopy and GC-MS. 2.20 mmol of 1,2-bis(trifluoroacetyl)ethane was formed. $^1H$ NMR (d)=ethylene glycol: 4.49 (4H, $H_2C$— $O_2CCF_3$). Reactions without added chloride also lead to similar reactivity. Under the same conditions these reactions yielded 11% glycol and 21% of what is tentatively assigned as 1-trifluoroacetyl-2-iodoethane. $^1H$ NMR (d)=1-trifluoroacetyl-2-iodoethane: 4.44 (2H, $H_2C$—$O_2CCF_3$, t, $^3J_{H-H}$=6.8 Hz); 3.17 (2H, $H_2C$—I, t, $^3J_{H-H}$=6.8 Hz)

Propane Functionalization:

In a typical reaction with propane a stir bar, 0.676 mmol KCl, 7.7 mmol $NH_4IO_3$ and 8.0 mL of HTFA were loaded into the reactor. After the reactor was sealed, it was purged 3 times with propane and finally charged with 830 kPa propane (3.0 mmol propane). The reactor was weighed and subsequently heated and stirred (800 rpm) for 2 h. The reactor was removed from the heating block, cooled to room temp. The resultant gas was collected in a gas bag and analyzed by GC-TCD. A standard of 30 mL of HOAc was added to the reaction liquid. The mixture was stirred, after which a sample was removed for centrifugation. The products were analyzed and indentified by $^1H$ NMR and GC-MS. 121 mmol of 1-trifluoroacetopropane, 404 mmol of 2-trifluoroacetopropane and 236 mmol of bis(1,2-trifluoroaceto) propane were formed in the reaction. $^1H$ NMR (d)=1-trifluoroacetopropane 4.17 (2H, $H_2C$—$O_2CCF_3$, t, $^3J_{H-H}$=7 Hz), 1.59 (2H, $CH_2CH_3$, m) 0.79 (3H, $CH_3$, t, $^3J_{H-H}$=7 Hz); 2-trifluoroacetopropane 4.17 (1H, HC—$O_2CCF_3$, h, $^3J_{H-H}$=6 Hz), 1.18 (6H, $CH_3$, d, $^3J_{H-H}$=6 Hz); bis-(1,2-trifluoroaceto) propane. 5.27 (1H, HC—$O_2CCF_3$, m), 4.38 (1H, $H_2C$— $O_2CCF_3$, dd, $^2J_{H-H}$=12 Hz, $^3J_{H-H}$=3 Hz), 4.27 (1H, $H_2C$— $O_2CCF_3$, dd, $^2J_{H-H}$=12 Hz, $^3J_{H-H}$=7 Hz), 1.26 (3H, $CH_3$, d, $^3J_{H-H}$=7 Hz).

REFERENCES (1) *BP Statistical Review of World Energy* 2013, BP, 2013.
(2) *Liquefied Natural Gas: Understanding the Basic Facts*, U. S. Department of Energy, 2005.
(3) World Bank Sees Warning Sign in Gas Flaring Increase, World Bank, 2012. http://www.worldbank.org/en/news/press-release/2012/07/03/world-bank-sees-warning-sign-gas-flaring-increase accessed Dec. 12, 2013.
(4) Olah, G. A.; Goeppert, A.; Prakash, G. K. S. *Beyond Oil and Gas: The Methanol Economy*; 2nd ed.; Wiley-VCH, 2009.
(5) Luo, Y.-R. In *Comprehensive Handbook of Chemical Bond Energies*; CRC Press: New York, N.Y., 2007, 19-145.
(6) Labinger, J. A. *J. Mol. Catal.* A 2004, 220, 27-35.
(7) Cavaliere, V. N.; Wicker, B. F.; Mindiola, D. J. In *Advances in Organometallic Chemistry*; Anthony, F. H., Mark, J. F., Eds.; Academic Press: 2012; Volume 60, 1-47.

(8) Webb, J. R.; Bolano, T.; Gunnoe, T. B. *ChemSusChem* 2011, 4, 37-49.
(9) Periana, R. A.; Bhalla, G.; Tenn Iii, W. J.; Young, K. J. H.; Liu, X. Y.; Mironov, O.; Jones, C. J.; Ziatdinov, V. R. *J. Mol. Catal. A* 2004, 220, 7-25.
(10) Stahl, S. S.; Labinger, J. A.; Bercaw, J. E. *Angew. Chem., Int. Ed.* 1998, 37, 2180-2192.
(11) Shilov, A. E.; Shul'pin, G. B. *Chem. Rev.* 1997, 97, 2879-2932.
(12) Bal'zhinimaev, B. S.; Paukshtis, E. A.; Kovalev, E. V.; Suknev, A. P.; Shalygin, A. S. (Uchrezhdenie RAN Institut Kataliza im. G. K. Boreskova SO RAN.). Method of selective catalytic oxychlorination of methane to methyl chloride. RU Patent 2446881C2, Apr. 10, 2012.
(13) Aglulin, A. G. *Kinet. Catal.* 2009, 50, 427-434.
(14) Stauffer, J. E. Process for the chlorination of methane. World Patent 9008117A1, Jul. 26, 1990.
(15) Rozanov, V. N.; Gvozd, E. V.; Kernerman, V. A.; Svetlanov, E. B.; Trushechkina, M. A.; Treger, Y. A. *Kinet. Katal.* 1989, 30, 148-154.
(16) Riegel, H.; Schindler, H. D.; Sze, M. C. (CE Lummus). Oxychlorination of methane. U.S. Pat. No. 4,207,268A, Jun. 10, 1980.
(17) Joseph, W. J.; Bianchi, A. B. (Dow Chemical). Manufacture of chlorinated hydrocarbons. U.S. Pat. No. 2,752,401, Jun. 26, 1956.
(18) Podkolzin, S. G.; Stangland, E. E.; Jones, M. E.; Peringer, E.; Lercher, J. A. *J. Am. Chem. Soc.* 2007, 129, 2569-2576.
(19) Brickey, R. T.; Lisewsky, G. A.; Waycuilis, J. J.; York, S. D. (Marathon GTF Technology, Ltd.). Processes for converting gaseous alkanes to liquid hydrocarbons using microchannel reactor. World Patent 2011159490A1, Dec. 22, 2011.
(20) Lorkovic, I. M.; Sun, S.; Gadewar, S.; Breed, A.; Macala, G. S.; Sardar, A.;
Cross, S. E.; Sherman, J. H.; Stucky, G. D.; Ford, P. C. *J. Phys. Chem. A* 2006, 110, 8695-8700.
(21) Olah, G. A.; Gupta, B.; Felberg, J. D.; Ip, W. M.; Husain, A.; Karpeles, R.; Lammertsma, K.; Melhotra, A. K.; Trivedi, N. J. *J. Am. Chem. Soc.* 1985, 107, 7097-7105.
(22) Ding, K.; Metiu, H.; Stucky, G. D. *ACS Catal.* 2013, 3, 474-477.
(23) Gunay, A.; Theopold, K. H. *Chem. Rev.* 2010, 110, 1060-1081.
(24) Nelson, A. P.; DiMagno, S. G. *J. Am. Chem. Soc.* 2000, 122, 8569-8570.
(25) Gormisky, P. E.; White, M. C. *J. Am. Chem. Soc.* 2013, 135, 14052-14055.
(26) Stoian, S. A.; Xue, G.; Bominaar, E. L.; Que, L.; Munck, E. *J. Am. Chem. Soc.* 2013, 136, 1545-1558.
(27) Hintermair, U.; Sheehan, S. W.; Parent, A. R.; Ess, D. H.; Richens, D. T.; Vaccaro, P. H.; Brudvig, G. W.; Crabtree, R. H. *J. Am. Chem. Soc.* 2013, 135, 10837-10851.
(28) Liu, W.; Huang, X.; Cheng, M.-J.; Nielsen, R. J.; William A. Goddard, I.; Groves, J. T. *Science* 2012, 337, 1322-1325.
(29) Liu, W.; Groves, J. T. *Angew. Chem., Int. Ed.* 2013, 52, 6024-6027.
(30) Liu, W.; Groves, J. T. *J. Am. Chem. Soc.* 2010, 132, 12847-12849.
(31) *Alkane C-H Activation by Single-Site Metal Catalysis*; Springer Netherlands, 2012; 38.
(32) *Activation and Functionalization of C—H Bonds*; American Chemical Society: Washington, D C, 2004.

(33) Gunnoe, T. B. In *Physical Inorganic Chemistry: Reactions, Processes, and Applications* Bakac, A., Ed.; John Wiley & Sons Inc.: Hoboken, N.J., 2010; 2, 495-549.
(34) Owen, J. S.; Labinger, J. A.; Bercaw, J. E. *J. Am. Chem. Soc.* 2006, 128, 2005-2016.
(35) Asbury, J. B.; Hang, K.; Yeston, J. S.; Cordaro, J. G.; Bergman, R. G.; Lian, T. *J. Am. Chem. Soc.* 2000, 122, 12870-12871.
(36) Crabtree, R. H. *Chem. Rev.* 2011, 112, 1536-1554.
(37) Choi, J.; MacArthur, A. H. R.; Brookhart, M.; Goldman, A. S. *Chem. Rev.* 2011, 111, 1761-1779.
(38) Crabtree, R. H.; Mihelcic, J. M.; Quirk, J. M. *J. Am. Chem. Soc.* 1979, 101, 7738-7740.
(39) Dobereiner, G. E.; Yuan, J.; Schrock, R. R.; Goldman, A. S.; Hackenberg, J. D. *J. Am. Chem. Soc.* 2013, 135, 12572-12575.
(40) Renkema, K. B.; Kissin, Y. V.; Goldman, A. S. *J. Am. Chem. Soc.* 2003, 125, 7770-7771.
(41) Leitch, D. C.; Lam, Y. C.; Labinger, J. A.; Bercaw, J. E. *J. Am. Chem. Soc.* 2013, 135, 10302-10305.
(42) Ahuja, R.; Punji, B.; Findlater, M.; Supplee, C.; Schinski, W.; Brookhart, M.; Goldman, A. S. *Nat. Chem.* 2011, 3, 167-171.
(43) Chepaikin, E. G. *Russ. Chem. Rev.* 2011, 80, 363-396.
(44) Jones, C. J.; Taube, D.; Ziatdinov, V. R.; Periana, R. A.; Nielsen, R. J.; Oxgaard, J.; Goddard, W. A., III *Angew. Chem., Int. Ed.* 2004, 43, 4626-4629.
(45) Periana, R. A.; Taube, D. J.; Gamble, S.; Taube, H.; Satoh, T.; Fujii, H. *Science* 1998, 280, 560-564.
(46) Periana, R. A.; Taube, D. J.; Taube, H.; Evitt, E. R. (Catalytica, Inc.). Catalytic process for converting lower alkanes to esters, alcohols, and to hydrocarbons. U.S. Pat. No. 5,306,855A, Apr. 26, 1994.
(47) Kao, L. C.; Hutson, A. C.; Sen, A. *J. Am. Chem. Soc.* 1991, 113, 700-701.
(48) Hashiguchi, B. G.; Konnick, M. M.; Bischof, S. M.; Gustafson, S. J.; Devarajan, D.; Gunsalus, N.; Ess, D. H.; Periana, R. A. *Science* 2014, 343, 1232-1237.
(49) Strassner, T.; Ahrens, S.; Muehlhofer, M.; Munz, D.; Zeller, A. *Eur. J. Inorg. Chem.* 2013, 2013, 3659-3663.
(50) Chen, W.; Kocal, J. A.; Brandvold, T. A.; Bricker, M. L.; Bare, S. R.; Broach, R. W.; Greenlay, N.; Popp, K.; Walenga, J. T.; Yang, S. S.; Low, J. J. *Catal. Today* 2009, 140, 157-161.
(51) Sen, A.; Greta, E.; Oliver, T. F. *Prepr.—Am. Chem. Soc., Div. Pet. Chem.* 1988, 33, 460-462.
(52) Flores, J. A.; Komine, N.; Pal, K.; Pinter, B.; Pink, M.; Chen, C.-H.; Caulton, K. G.; Mindiola, D. J. *ACS Catal.* 2012, 2, 2066-2078.
(53) Caballero, A.; Despagnet-Ayoub, E.; Mar Díaz-Requejo, M.; Diaz-Rodriguez, A.; González-Núñez, M. E.; Mello, R.; Muñoz, B. K.; Ojo, W.-S.; Asensio, G.; Etienne, M.; Pérez, P. J. *Science* 2011, 332, 835-838.
(54) Zhdankin, V. V.; Stang, P. J. *Chem. Rev.* 2008, 108, 5299-5358.
(55) Richardson, R. D.; Wirth, T. *Angew. Chem., Int. Ed.* 2006, 45, 4402-4404.
(56) Wirth, T. *Angew. Chem., Int. Ed.* 2005, 44, 3656-3665.
(57) Dohi, T.; Kita, Y. *ChemCatChem* 2014, 6, 76-78.
(58) Moteki, S. A.; Usui, A.; Zhang, T.; Solorio Alvarado, C. R.; Maruoka, K. *Angew. Chem., Int. Ed.* 2013, 52, 8657-8660.
(59) Ding, K.; Zhang, A.; Stucky, G. D. *ACS Catal.* 2012, 2, 1049-1056.
(60) Buddrus, J.; Plettenberg, H. *Angew. Chem., Int. Ed.* 1976, 15, 436-436.

(61) Michalkiewicz, B.; Jarosinska, M.; Lukasiewicz, I. Chem. Eng. J. 2009, 154, 156-161.
(62) Gang, X.; Zhu, Y.; Birch, H.; Hjuler, H. A.; Bjerrum, N. J. App. Cat. A: Gen. 2004, 261, 91-98.
(63) Periana, R. A.; Mirinov, O.; Taube, D. J.; Gamble, S. Chem. Commun. 2002, 2376-2377.
(64) Bjerrum, N. J.; Xiao, G.; Hjuler, H. A. (Statoil Research Centre). Process and catalyst system for the oxidation of gaseous hydrocarbons into alcohols. World Patent 9924383A1, May 20, 1999.
(65) Kuck, M. A. A novel process for the oxychlorination of ethane. U.S. Pat. No. 3,987,118 A, Oct. 19, 1976.
(66) Golden, D. M.; Benson, S. W. Chem. Rev. 1969, 69, 125-134.
(67) Stewart, P. H.; Larson, C. W.; Golden, D. M. Combust. Flame 1989, 75, 25-31.
(68) Stolarov, I. P.; Vargaftik, M. N.; Shishkin, D. I.; Moiseev, I. I. J. Chem. Soc., Chem. Commun. 1991, 938-939.
(69) Daehlie, G.; Kjekshus, A. Acta Chem. Scand. 1964, 18, 144-156.
(70) Jansen, M.; Miller, R. Angew. Chem., Int. Ed. 1997, 36, 255-256.
(71) Dasent, W. E.; Waddington, T. C. J. Chem. Soc. 1960, 3350-3356.
(72) Conley, B. L.; Tenn, W. J.; Young, K. J. H.; Ganesh, S. K.; Meier, S. K.; Ziatdinov, V. R.; Mironov, O.; Oxgaard, J.; Gonzales, J.; Goddard, W. A.; Periana, R. A. J. Mol. Catal. A: Chem. 2006, 251, 8-23.
(73) Schumacher, J. C. Chem. Eng. Prog. 1960, 56, 83-84.
(74) Hawkins, M.; Andrews, L.; Downs, A. J.; Drury, D. J. J. Am. Chem. Soc. 1984, 106, 3076-3082.
(75) Webb, J. R.; Burgess, S. A.; Cundari, T. R.; Gunnoe, T. B. Dalton. Trans. 2013, 42, 16646-16665.
(76) Slaughter, L. M.; Wolczanski, P. T.; Klinckman, T. R.; Cundari, T. R. J. Am. Chem. Soc. 2000, 122, 7953-7975.
(77) Walsh, P. J.; Hollander, F. J.; Bergman, R. G. J. Am. Chem. Soc. 1988, 110, 8729-8731.
(78) Handbook of Chemical Health and Safety; American Chemical Society, 2001.
(79) Chemical Saftey Practices & Recommendations, 2013. http://www.acs.org/content/acs/en/about/governance/committees/chemicalsafety/safetypractices.html accessed
(80) Hickey, D. M. B.; Leeson, P. D.; Novelli, R.; Shah, V. P.; Burpitt, B. E.; Crawford, L. P.; Davies, B. J.; Mitchell, M. B.; Pancholi, K. D.; et, a. J. Chem. Soc., Perkin Trans. 1 1988, 3103-3111.

Example 18

Hydrocarbon Functionalization Using Iodine Oxide and Chloride Salts Under Photolytic Conditions The use of mixtures of iodate or periodate salts with chloride for the thermal functionalization of methane, ethane, and propane have been previously reported.[1,2] These reactions are highly selective for the production of the corresponding alkyl esters as well as some alkyl halide, which are protected from over-oxidation. For these processes, the highest reported yield of methyl trifluoroacetate (MeTFA) was 42% relative to methane, which was obtained in the optimized reaction of potassium periodate with potassium chloride in trifluoroacetic acid (HTFA).[2]

Recent efforts have focused on the extension of this chemistry to photolytic reaction conditions using a mercury arc lamp. After 24 h of photolysis, ~20% yield of MeTFA was obtained relative to methane, with <0.5% yield of MeCl when using 0.67 mmol KCl, 7.7 $NH_4IO_3$, 8 mL HTFA, and 100 psi of methane. With periodate, the MeCl yield was similar but the MeTFA yield was slightly lower, 15% rather than 20%. Accordingly, iodate was the primary focus of further studies. By increasing the chloride loading to 2.01 mmol, the yield of MeTFA increases to 25% with 2% yield of MeCl. Lowering the methane pressure to 50 psi and increasing the reaction time to 48 h gave ~50% yield of MeTFA, higher than that obtained under the optimal thermal conditions. Additionally, product concentrations of >1 M are observed. Various solvents were examined for the reaction (FIG. 6.1). Dilute HTFA (3:1 mol/mol HTFA/$H_2O$) gave lower MeTFA yields, 15% rather than 25% relative to neat HTFA, but indicated that the presence of water does not compromise the reaction. A weaker acid, dichloroacetic acid, gave similar results to the dilute HTFA, further indicating that a relatively strong acid such as HTFA is not required for the reaction.

Ethane and propane were also tested for photolytic functionalization to examine the substrate scope (FIG. 7.1). Under these conditions with methane, a ~25% total yield was obtained, with >95% selectivity for MeTFA. The yield of EtTFA in the ethane functionalization reaction is similar, and high selectivity, ~90%, is also observed. However, propane functionalization is much less selective and gives significantly lower yields. Compact fluorescent light (CFL) has also been demonstrated to be effective with methane, demonstrating that visible light can be used to functionalize light alkanes. As shown in FIG. 8.1, a 500 W CFL bulb can be used to promote the functionalization of methane in the presence of iodate and chloride.

REFERENCES 1. 1. Fortman, G. C.; Boaz, N. C.; Munz, D.; Konnick, M. M.; Periana, R. A.; Groves, J. T.; Gunnoe, T. B. J. Amer. Chem. Soc. 2014, 136, 8393-8401.
2. Kalman, S. E.; Munz, D.; Fortman, G. C.; Boaz, N. C.; Groves, J. T.; Gunnoe, T. B. Dalton Trans. 2015, 44, 5294-5298.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A method, comprising:
   mixing $A_aX_n$, an iodine-based compound, and a source of functionalization to form a first mixture, wherein A is selected from the group consisting of: hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$) and a combination thereof, wherein X is chlorine or bromine, wherein subscript "a" is an oxidation state of X and subscript "n" is an oxidation state of A;
   mixing the first mixture with a hydrocarbon in the gas phase to form a second mixture; and
   applying light from a light source to the second mixture to make a functionalized hydrocarbon.

2. The method of claim 1, further comprising:
   converting the functionalized hydrocarbon to a compound including at least one group selected from the group consisting of: hydroxyl, halide, carbonyl, and a combination thereof.

3. The method of claim 2, wherein the compound is selected from an alcohol or glycol.

4. The method of claim 2, wherein the compound is methanol, ethanol, or propanol.

5. The method of claim 1, wherein the hydrocarbon is selected from the group consisting of: methane, ethane, propane, butane, and a combination thereof.

6. The method of claim 1, wherein the hydrocarbon is aliphatic.

7. The method of claim 1, wherein the hydrocarbon is aromatic.

8. The method of claim 1, wherein $A_aX_n$ is selected from the group consisting of: HCl, NaCl, KCl, $CaCl_2$, LiCl, $ZnCl_2$, $BeCl_2$, $MgCl_2$, $PCl_3$, $NH_4Cl$, 0014, $CHCl_3$, transition metal chlorides, main group metal chlorides or organochlorides, or combination thereof.

9. The method of claim 1, wherein A is selected from the group consisting of: hydrogen, lithium, sodium, potassium, beryllium, magnesium, calcium, strontium, barium, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$) and a combination thereof.

10. The method of claim 1, wherein the iodine-based compound is selected from the group consisting of: iodate, periodate, iodine oxide, iodosyl ($IO^+$), trivalent iodine compound, and a combination thereof.

11. The method of claim 1, wherein the iodine-based compound is $Q(IO_3)_p$, wherein Q is selected from the group consisting of: hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, and trimethyl sulfonium ($[S(CH_3)_3]^+$), wherein "p" is 1 to 5.

12. The method of claim 1, wherein the iodine-based compound is selected from the group consisting of: $KIO_3$, $Ca(IO_3)_2$, $Ba(IO_3)_2$, $Cu(IO_3)_2$, $NH_4IO_3$, $H_5IO_6$, $KIO_4$, $NaIO_4$ and $NH_4IO_4$, $I(TFA)_3$, $I_2O_5$, $[IO]^+$, $[IO_2]^+$, and combination thereof.

13. The method of claim 1, wherein the source of functionalization is selected from the group consisting of: trifluoroacetic acid, trifluoroacetic anhydride, hexafluorobutyric acid, water, sulfuric acid, acetic acid, supercritical carbon dioxide, phosphoric acids, and a combination thereof.

14. The method of claim 1, wherein the light form the light source is applied to the second mixture for a period of time of about 24 hours to about 72 hours.

15. The method of claim 1, wherein mixing the first mixture with the hydrocarbon is conducted at an internal pressure of about 15 to 1500 psi and at a temperature of about 25 to 300° C. for about 10 minutes to 5 days.

16. The method of claim 1, wherein $A_aX_n$ is about 0.2 to 25 weight % of the first mixture, wherein the iodine-based compound is about 2 to 40 weight % of the first mixture, wherein the source of functionalization is about 30 to 95 weight % of the first mixture, and wherein the amount of the hydrocarbon relative to the first mixture is about 0.01 to 20 weight %.

17. The method of claim 1, wherein the mass of $A_aX_n$ relative to the source of functionalization is about 0.14 to 10% and wherein the mass of the iodine-based compound relative to the source of functionalization is about 17 to 26%.

18. A system for producing a functionalized hydrocarbon, comprising:
   a vessel including $A_aX_n$, an iodine-based compound, and a source of functionalization to form a first mixture and a hydrocarbon, wherein A is selected from the group consisting of: hydrogen, lithium, sodium, potassium, beryllium, magnesium, calcium, strontium, barium, transition metals, aluminum, gallium, thallium, indium, tin, sulfur, ammonium ($NH_4^+$), alkylammonium, phosphonium ($PH_4^+$), alkylphosphonium, arylphosphonium, or trimethyl sulfonium ($[S(CH_3)_3]^+$) and a combination thereof, wherein X is chlorine or bromine, wherein "a" is the oxidation state of X and "n" is the oxidation state of A;
   wherein the vessel further comprises a light source.

19. The system of claim 18, wherein the light source is a mercury arc lamp or a compact fluorescent light bulb.

20. The system of claim 18, wherein the vessel further comprises a pressure system to pressurize the vessel to about 15 to 1500 psi, a heating system to heat the vessel to about 25 to 300° C., or both.

* * * * *